(12) United States Patent
Yoon et al.

(10) Patent No.: US 9,719,134 B2
(45) Date of Patent: Aug. 1, 2017

(54) MICRODROPLET-MANIPULATION SYSTEMS AND METHODS FOR AUTOMATED EXECUTION OF MOLECULAR BIOLOGICAL PROTOCOLS

(71) Applicant: The Arizona Board of Regents on Behalf of the University of Arizona, Tucson, AZ (US)

(72) Inventors: Jeong-Yeol Yoon, Tucson, AZ (US); David J. You, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/512,256

(22) Filed: Oct. 10, 2014

(65) Prior Publication Data
US 2015/0104798 A1    Apr. 16, 2015

Related U.S. Application Data

(63) Continuation of application No. 13/816,648, filed as application No. PCT/US2011/050553 on Sep. 6, 2011, now abandoned.
(Continued)

(51) Int. Cl.
*C12Q 1/68*    (2006.01)
*B01L 3/00*    (2006.01)
(Continued)

(52) U.S. Cl.
CPC ............... *C12Q 1/686* (2013.01); *B01L 7/52* (2013.01); *G01N 35/1009* (2013.01); *G01N 2035/1037* (2013.01)

(58) Field of Classification Search
None
See application file for complete search history.

(56) References Cited

U.S. PATENT DOCUMENTS

5,443,791 A * 8/1995 Cathcart ............ G01N 35/0098
                                                       422/561
5,486,337 A    1/1996 Ohkawa
(Continued)

FOREIGN PATENT DOCUMENTS

WO    WO 01/34842    5/2001
WO    WO 01/47638    7/2001
(Continued)

OTHER PUBLICATIONS

Mumm et al "Easy route to superhydrophobic compper-based wire-guided droplet microfluidic systems" ACS Nano,Aug. 14, 2009, 3(9): 2647-2652.*
(Continued)

*Primary Examiner* — Betty Forman
(74) *Attorney, Agent, or Firm* — Klarquist Sparkman, LLP

(57) ABSTRACT

Disclosed herein are automated systems for performing various biochemical and molecular biological procedures, including processor-controlled execution of protocols involving multiple steps performed in, on, or with liquid microdroplets. Example protocols are the various Polymerase Chain Reaction (PCR) protocols, but the subject systems are not limited to performing PCR protocols. Formation of a microdroplet of the sample for use in the described systems is achieved by bringing an amount of the sample into contact with a hydrophobic milieu, such as a superhydrophobic surface or hydrophobic liquid.

26 Claims, 10 Drawing Sheets

Related U.S. Application Data

(60) Provisional application No. 61/402,901, filed on Sep. 7, 2010.

(51) Int. Cl.
 *G01N 35/10* (2006.01)
 *B01L 7/00* (2006.01)

(56) References Cited

U.S. PATENT DOCUMENTS

| | | |
|---|---|---|
| 2002/0001546 A1 | 1/2002 | Hunter et al. |
| 2002/0143167 A1 | 10/2002 | Kondow et al. |
| 2007/0059763 A1 | 3/2007 | Okano et al. |
| 2007/0207272 A1 | 9/2007 | Puri et al. |
| 2008/0213853 A1 | 9/2008 | Garcia et al. |
| 2009/0280475 A1* | 11/2009 | Pollack ............... C12Q 1/6869 435/6.11 |
| 2009/0289213 A1* | 11/2009 | Pipper ............... B01J 20/28009 252/62.51 R |

FOREIGN PATENT DOCUMENTS

| | | |
|---|---|---|
| WO | WO 01/88525 | 11/2001 |
| WO | WO 2004/103891 | 12/2004 |
| WO | WO 2007/087690 | 8/2007 |
| WO | WO 2010/017671 | 2/2010 |
| WO | WO 2010/040214 | 4/2010 |

OTHER PUBLICATIONS

Chien et al "A micro circulating PCR chip using a suction-type membrane for fluidic transport" Biomed Microdevices, Oct. 31, 2008 11: 359-367.*

International Search Report and Written Opinion of the International Searching Authority, mailed Dec. 1, 2011, for corresponding International Application No. PCT/US2011/050553, 13 pages.

Lindsay et al., "Discrete microfluidics with electrochemical detection," *Analyst*, 132(5):412-416 (Abstract only, 4 pages), 2007.

Yoon et al., "Backscattering particle immunoassays in wire-guide droplet manipulations," *Journal of Biological Engineering*, 2:15, 12 pages, 2008.

* cited by examiner

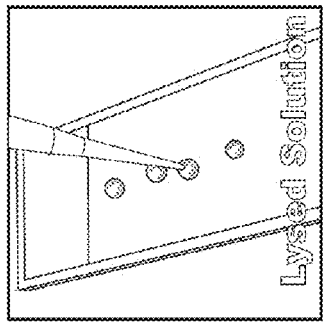
FIG. 7A Concentrated Sample
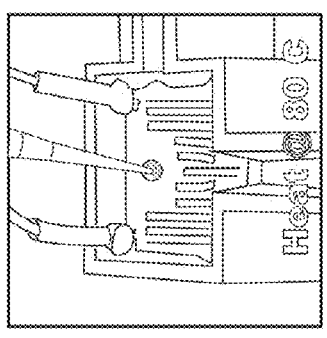
FIG. 7B Add Cell Lysis
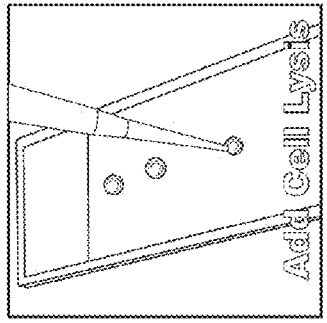
FIG. 7C Heat @ 80 C
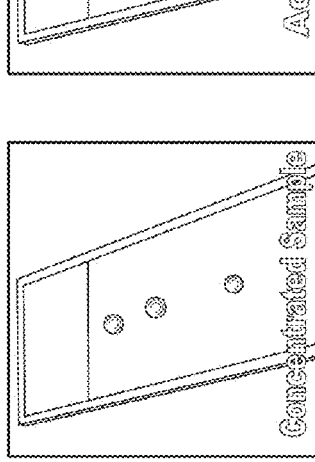
FIG. 7D Lysed Solution
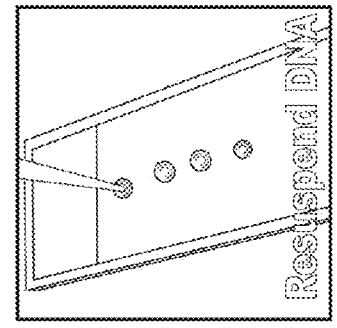
FIG. 7E Add IPA
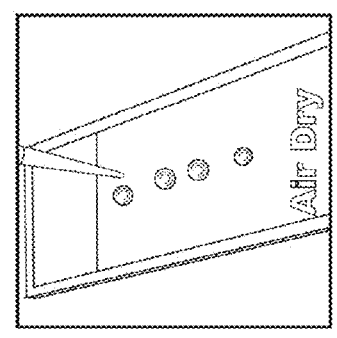
FIG. 7F Wash in EtOH
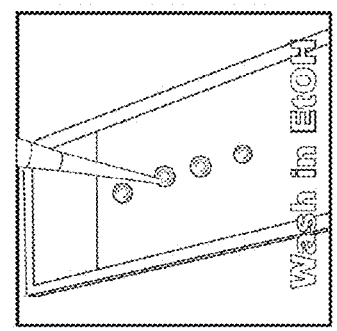
FIG. 7G Air Dry
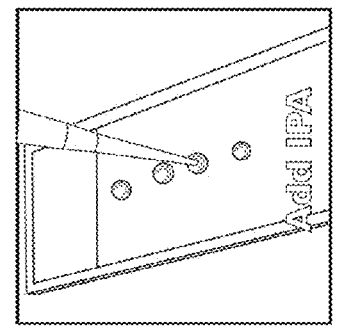
FIG. 7H Resuspend DNA

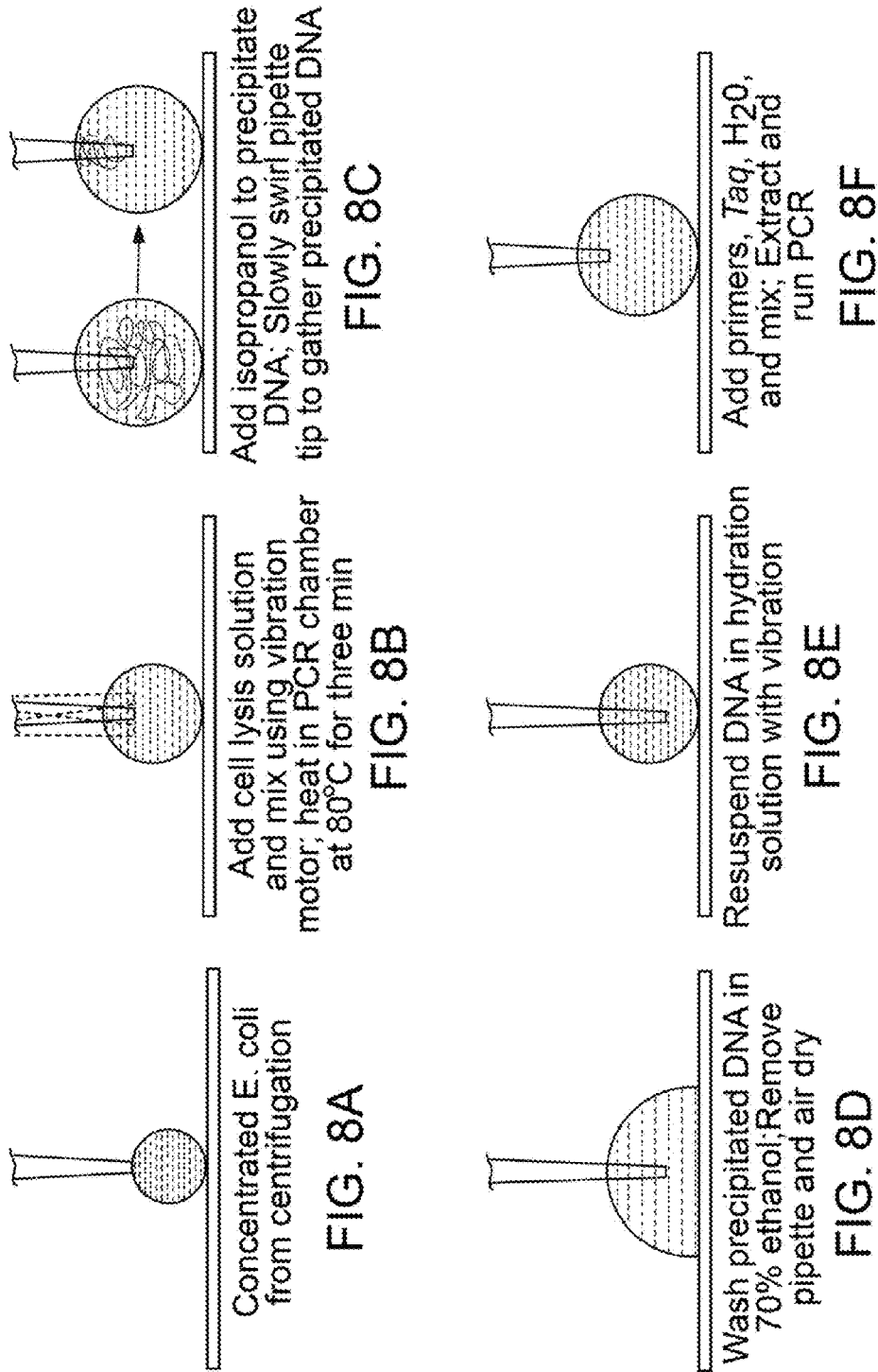

MICRODROPLET-MANIPULATION SYSTEMS AND METHODS FOR AUTOMATED EXECUTION OF MOLECULAR BIOLOGICAL PROTOCOLS

CROSS-REFERENCE TO RELATED APPLICATIONS

This application is a continuation of U.S. patent application Ser. No. 13/816,648, filed Feb. 12, 2013 which is the U.S. National Stage of International Application No. PCT/US2011/050553, filed Sep. 6, 2011, which in turn claims priority to and the benefit of U.S. Provisional Patent Application No. 61/402,901, filed on Sep. 7, 2010, both of which are incorporated herein by reference in their respective entireties.

FIELD

This disclosure pertains to, inter alia, automated systems for performing various biochemical and molecular biological procedures, including processor-controlled execution of protocols involving multiple steps performed in, on, or with liquid microdroplets. Example protocols are the various Polymerase Chain Reaction (PCR) protocols, but the subject systems are not limited to performing PCR protocols.

BACKGROUND

Most protocols used in biochemistry and molecular biology comprise multiple steps that must be executed properly and in the proper order. Exemplary steps include mixing, diluting, centrifuging, separating, extracting, suspending, heating, cooling, reacting, dispensing, and the like. Many of these steps are similar, at least in part, in various protocols. A principal difference of one protocol versus another is often the particular order in which the steps are executed. Another difference is a different value of a parameter (e.g., temperature or reaction time) in one protocol versus another. Yet another difference is the inherent variability of different people performing nominally similar steps.

An example of a molecular biological protocol involving a defined series of steps, in which most of the steps are repeated multiple times, is the Polymerase Chain Reaction (PCR) protocol. Since its inception, PCR has been modified and tailored for use in multiple specific situations. Consequently, although there are currently multiple PCR protocols, many of the steps in them are substantially the same because, for example, substantially all existing protocols involve performing multiple temperature "cycles." This has generated interest in automating PCR protocols. In addition, there have been attempts to derive PCR protocols that use progressively smaller sample and reagent volumes and that can perform a PCR cycle in less time.

For example, there have been various attempts to incorporate the complete process of PCR assays into microchannels, using microfluidics, to reduce sample volumes. Since a microchannel is a fluid passageway formed with a specific configuration, it cannot be changed easily to accommodate departures from the particular protocol for which the microchannel was configured. Consequently, a key problem with this approach is that the user cannot change the assay protocol easily. Also, the small size of the microchannel device complicates isolating the different locations at which respective thermal steps in the PCR cycle are conducted, and prevent the removal and characterization of sample aliquots at any stage in the PCR cycle.

Decreasing the sample size inevitably involves the production and manipulation of small droplets (e.g., "microdroplets") of liquid. In the various efforts at automating laboratory procedures, manipulating small droplets has been the focus of much attention in recent years. Berthier and Silberzan, *Microfluidics for Biotechnology*, Artech House, Norwood, 2006. Use of small droplets allows significantly smaller reaction volumes and decreased assay times. The two primary modes of conventional droplet manipulations are: (1) manipulating discrete liquid plugs in pre-defined microchannels (Belder, *Angew. Chem. Int. Ed.* 44:3521-3522, 2005; Joanicot and Ajdari, *Science* 309:887-888, 2005), and (2) manipulating liquid droplets resting on an open, flat surface (Mugele and Baret, *J. Phys: Condens. Matter* 17:R705-R774, 2005; Su et al., *ACM Trans. Design Autom. Electron Syst.* 11:442-464, 2006). The first mode (1) incorporates "liquid plug" techniques and the second mode (2) incorporates "open-surface" techniques. Changing an automated liquid-plug technique is difficult essentially because changing the technique involves changing the microfluidic plumbing. Open-surface techniques, involving the manipulation of liquid droplets on an open, flat surface, has been demonstrated most notably in association with magnetofluidics, in which the droplets containing paramagnetic particles move over a hydrophobic surface under the influence of an external magnetic field. Egatz-Gomez et al., *Appl. Phys. Lett.* 89:034106, 2006. A difficulty with this technique is that paramagnetic particles have not yet been designed that do not interfere with biological reactions. Another technique in this general category is called electrowetting on dielectrics ("EWOD"). Cho et al., *J. Microelectromech. Syst.* 12:70-80, 2003. Although this technique allows precise droplet movement, splitting, and merging, an apparatus performing this method is comparatively difficult to fabricate and operate, and has problems with diffusional mixing and contamination from increased wetting on the surface. Thus, a continuing need exists for improved systems and methods of manipulating biological liquids in a microfluidic environment.

SUMMARY

Disclosed herein are methods and apparatus for performing, in a controlled and programmed automatic manner, various protocols on microdroplet-sized samples of hydrophilic liquids. The protocols are particularly directed to respective processes performed in biochemical and/or molecular biological investigations. The protocols are executed by respective steps involving respective manipulations of microdroplets.

Formation of a microdroplet of the sample is achieved by bringing an amount of the sample into contact with a "hydrophobic milieu." As the amount of the sample interacts with the hydrophobic milieu, a microdroplet of the sample is formed. The microdroplet form is retained as long as it remains in contact with the hydrophobic milieu. One form of the hydrophobic milieu is a superhydrophobic surface on which the sample forms microdroplets having a contact angle of at least 150° but desirably close to, but no greater than, 180°. Another form of the hydrophobic milieu is a hydrophobic liquid in which the sample is immersed to form the microdroplet. With respect to either milieu, the microdroplet retains its microdroplet form so long as it remains in contact with the respective milieu.

The volume of a particular microdroplet is substantially unlimited in terms of minimal volume. In other words, the microdroplets can be as small as desired, so long as they can be manipulated. Maximum volume of a microdroplet is determined by the particular volume limit past which the microdroplet is no longer substantially spherical. Depending upon the particular sample and particular hydrophobic milieu, the maximum volume can range from about 20 µL to about 100 µL, more typically in the range of 20-50 µL.

The protocols can be any of various "wet" processes that can be performed on a chemical or biological sample, such as a sample collected in the field or a sample produced in a laboratory. In an advantageous embodiment the processes are of generally two types: thermocycling protocols and pre-thermocycling protocols. Not intending to be limiting, an important thermocycling protocol is one of the Polymerase Chain Reaction (PCR) protocols. Important pre-thermocycling protocols include, but are not limited to, dilutions of the sample, extraction of genetic material from the sample, centrifuging the sample, and extracting genetic material from the sample.

The systems are of a size permitting them to be placed on a benchtop, such as in a laboratory. Some embodiments are miniaturized to an extent that they can be taken into the field for on-site processing and identification of samples collected there.

PCR protocols performable using the subject apparatus are rapid compared to most conventional apparatus. A key reason for this speed is the inclusion, in many embodiments, of a thermocycling vessel or "PCR vessel" having multiple chambers each containing the hydrophobic liquid. The chambers have respective heaters and temperature sensors to provide respective volumes of the hydrophobic liquid at respective temperatures. In many embodiments three chambers are provided so as to provide a respective chamber for each of the temperatures normally required in a PCR cycle. The chambers are connected together by channels that also contain the hydrophobic liquid. The channels allow microdroplets to be transferred from chamber to chamber without being removed from the hydrophobic milieu.

The subject apparatus also include a "movement and placement device" to which a "microdroplet manipulation device" is coupled. The movement and placement device in many embodiments comprises a processor-controlled manipulator such as an x-y or x-y-z manipulator to which a block or member (called herein a "carriage") is mounted. In this disclosure the processor-controlled manipulator is also called a "wire-guide system" for reasons discussed elsewhere herein.

Formed microdroplets tend to remain as microdroplets so long as they remain in contact with their respective hydrophobic milieu. Substantially all the protocols performable using the system involve manipulations of one or more microdroplets. Example protocols include, but are not limited to, dilution of microdroplets (e.g., serial dilution), centrifugation of microdroplets in situ, extraction of DNA or other genetic material, and rapid PCR thermocycling. Depending upon the specific protocol, it is performed either on a superhydrophobic surface or in a hydrophobic liquid. Some protocols can be performed on either hydrophobic milieu. The system has substantially no limitations on the complexity and configuration of protocols that it can perform, making it extremely versatile and far-reaching in its applications.

The system can perform substantially any microdroplet-manipulation-based protocol pre-programmed into the system (more specifically into the controller). Modifications required for adding a protocol or changing a protocol are simply made by changing the programming, which can be easily accomplished by the operator. Because of this flexibility, the user has the ability to start and stop execution of a protocol at substantially any time, manually control the droplet-manipulation system, make adjustments to the protocol on-the-fly, and resume a suspended protocol where it left off. The system can be used to execute pre-programmed droplet movements and manipulations for the rapid detection of a particular microorganism by PCR. In such an application, the microdroplet movements and manipulations can include serial dilutions, centrifugation, extraction of genetic material from a droplet, and amplification of the genetic material by PCR thermocycling. As confirmed by post-PCR gel electrophoresis, the processes performed by the system produced greater positive band intensity over a non-centrifuged sample. Thus, the system has the adaptability to replace many common laboratory tasks on a single platform (through re-programmability), and rapid succession (using droplets) and with a high level of accuracy and automation.

It will be understood that the microdroplet-manipulating device may have a first portion that remains stationary and a second portion that is moved by the movement and placement device.

One aspect as disclosed herein is directed to apparatus as summarized above. An embodiment of such an apparatus comprises a movement and placement device having a range of movement in at least two dimensions (e.g., x and y, or x, y, and z). A microdroplet-manipulating device is coupled to the movement and placement device so as to be placeable by the movement and placement device within the range of movement. A hydrophobic milieu is located within the range of movement. A controller is operably connected to the movement and placement device and to the microdroplet-manipulating device. The controller is programmable with a protocol in which the movement and placement device is commanded to place the microdroplet-manipulating device relative to the hydrophobic milieu. The microdroplet-manipulating device is commanded to perform automatically at least two of the following: (a) placing an amount of a hydrophilic liquid in contact with the hydrophobic milieu sufficiently to form at least one microdroplet of the hydrophilic liquid on or in the hydrophobic milieu, (b) manipulating the microdroplet while the microdroplet is in contact with the hydrophobic milieu, and (c) removing at least a portion of a microdroplet from contact with the hydrophobic milieu.

In this embodiment the hydrophobic milieu can comprise: (1) a superhydrophobic surface, and (2) a hydrophobic liquid. These two milieu have different respective locations in the range of movement. In such an embodiment the controller is further programmed to command the microdroplet-manipulating device to place an amount of a first hydrophilic liquid on the superhydrophobic surface to form a first microdroplet on the superhydrophobic surface and to place an amount of a second hydrophilic liquid in the hydrophobic liquid to form a second microdroplet in the hydrophobic liquid. The controller can be further programmed to command the microdroplet-manipulating device to manipulate the first microdroplet on the superhydrophobic surface and to command the microdroplet-manipulating device to manipulate the second microdroplet in the hydrophobic liquid. The command to manipulate the first microdroplet on the superhydrophobic surface can be part of a first protocol, while the command to manipulate the second microdroplet in the hydrophobic liquid can be part of a second protocol. The first protocol can comprise extracting genetic material from a sample, and the second protocol can comprise amplifying a predetermined portion of the extracted genetic material, particularly by thermocycling.

By way of example, any of the following can be within the scope of manipulating the microdroplet on the superhydrophobic surface: (a) moving the microdroplet, (b) adding a substance to the microdroplet, (c) removing a substance from the microdroplet, (d) mixing contents of the microdroplet, (d) concentrating the microdroplet, (e) changing a composition of the microdroplet, (f) changing a position of the microdroplet, (g) holding a substance relative to the microdroplet, (h) merging the microdroplet with another microdroplet, (i) splitting the microdroplet, and (j) rotating the microdroplet.

By way of example, any of the following can be within the scope of manipulating the microdroplet in the hydrophobic liquid: (a) moving the microdroplet, (b) adding heat to the microdroplet, (c) removing heat from the microdroplet, (d) placing the microdroplet in a pendant condition relative to the hydrophobic liquid, and (e) retracting the microdroplet.

For performing thermocycling, the apparatus desirably includes a vessel that comprises at least three temperature-regulated chambers each containing a respective volume of the hydrophobic liquid at a respective temperature. In addition, the vessel desirably also comprises respective channels connecting the chambers together in a cyclical manner, wherein each channel also contains a respective volume of the hydrophobic liquid and the channels open into the respective chambers. Of these chambers, a first temperature-regulated chamber is one in which the hydrophobic liquid is at a nucleic acid-denaturation temperature. The second temperature-regulated chamber is one in which the hydrophobic liquid is at a nucleic acid annealing temperature, and the third temperature-regulated chamber is one in which the hydrophobic liquid is at a nucleic acid extension temperature. By way of example the denaturation temperature is in a range of about 94-96° C., the annealing temperature is in the range of about 50-65° C., and the extension temperature is in a range of about 70-74° C.

Desirably, the controller is further configured to command the movement and positioning device to move the microdroplet-manipulating device in a manner such that the microdroplet, while being kept submerged in the hydrophobic liquid, is moved from one chamber of the vessel to the next according to a preset thermal cycle. The controller desirably is further configured to command the microdroplet-manipulating device to hold the microdroplet in each chamber for a preset respective length of time. Further desirably, the microdroplet-manipulating device is configured to hold the microdroplet in each chamber while the microdroplet is pendant from the microdroplet-manipulating device and while the microdroplet-manipulating device moves the pendant droplet relative to the hydrophobic liquid to ensure good convective heating of the microdroplet. If required or as desired, the microdroplet-manipulating device is further configured to retract the microdroplet as the microdroplet-manipulating device is moving the microdroplet through a respective channel from one chamber to the next in the cycle. Also, the microdroplet-manipulating device is further configured to de-retract the microdroplet as the microdroplet is being held by the microdroplet-manipulating device in a subsequent chamber of the cycle.

In many of the manipulations summarized above, the microdroplet manipulating device is simply a small syringe (e.g., 1-mL capacity) fitted with a blunt hypodermic needle or pipetter tip. The pipetter tips are advantageous for many of the manipulations and offer the benefit of being inexpensive and commercially available in large quantities. The can also be arrayed at a rack or the like in the range of movement of the placement and movement device for automatic re-tipping as required.

Whereas most of the manipulations (e.g., performing dilutions) are readily understood, certain manipulations, such as "centrifuging" and "mixing" the contents of a microdroplet (particularly on the superhydrophobic surface) are surprising result obtained by appropriately "vibrating" the syringe and/or tip thereof. In many embodiments a "vibration motor" is placed adjacent the tip of the syringe and commanded to actuate (e.g., by a pulse-width-modulated drive signal) in a manner resulting in a stifling motion of the syringe tip, which appropriately agitates the microdroplet without breaking it up.

The foregoing and additional features and advantages of the subject of this disclosure will be more apparent from the following detailed description, which proceeds with reference to the accompanying drawings.

BRIEF DESCRIPTION OF THE DRAWINGS

FIG. 5A depicts placing multiple 20-µL microdroplets of diluent (phosphate-buffered saline (PBS)) on the superhydrophobic surface; FIG. 5B shows 2 µL of $E.$ $coli$ suspension being added to the first microdroplet for dilution; FIG. 5C shows the first microdroplet being mixed (mixing is performed by vibrating the syringe to which the pipetter tip is attached, which causes corresponding vibration of the syringe tip); FIG. 5D shows the syringe being withdrawn momentarily for retipping; FIG. 5E shows 2 µL being withdrawn from the first microdroplet for further dilution; FIG. 5F shows the withdrawn liquid from the first microdroplet being added to and mixed with the second microdroplet; FIG. 5G shows the syringe being withdrawn momentarily for retipping; and FIG. 5H shows the last microdroplet receiving a 2-µL aliquot from the third microdroplet, thereby producing a $10^{-4}$ dilution of the original $E.$ $coli$ suspension.

FIG. 6A shows a needle tip immersed in the microdroplet as a blunt, hollow needle is being induced to undergo circular motion relative to the superhydrophobic surface (motion is imparted by a vibration motor contacting the syringe and induced to vibrate in a desired manner by pulse-width modulation); FIG. 6B shows spinning of the microdroplet being induced by the vibrating needle (microdroplet spinning at 2264 rpm, which produces 22×g centrifugal force); FIG. 6C depicts liquid from the center of the microdroplet being drawn up by the needle; and FIG. 6D depicts the remaining microdroplet of concentrated sample remaining on the superhydrophobic surface after withdrawal of the needle.

FIGS. 7A-FH are a series of images of a protocol in which DNA is extracted from a microdroplet of a concentrated sample on the superhydrophobic surface. FIG. 7A shows a droplet (foremost microdroplet) of concentrated sample as placed on the superhydrophobic surface; FIG. 7B shows a pipetter tip adding cell-lysis solution to the microdroplet; FIG. 7C shows the microdroplet being heated (while submerged in silicone oil in a lysis chamber at 80° C., the silicone oil being another example of a hydrophobic milieu); FIG. 7D shows a microdroplet of the lysed solution being placed on the superhydrophobic surface; FIG. 7E shows isopropyl alcohol being added to the microdroplet of lysed cells to precipitate the DNA, wherein the precipitated DNA adheres to the pipetter tip; FIG. 7F shows the pipetter tip (with adhered DNA) being washed in a microdroplet of ethanol; FIG. 7G depicts the pipetter tip (with adhered DNA) being air-dried; and FIG. 7H shows the pipetter tip immersed in a hydration solution in which the DNA is resuspended.

FIGS. 8A-8F are schematic elevational views of respective steps in the protocol for DNA extraction shown in FIGS. 7A-7H. FIG. 8A shows the pipetter tip placing a microdroplet of concentrated E. coli produced in the centrifugation protocol (FIGS. 6A-6E) on the superhydrophobic surface; FIG. 8B shows cell-lysis solution being added to the microdroplet and mixed by vibrating the pipetter tip; FIG. 8C shows isopropanol being added to the microdroplet to precipitate to the DNA, and also shows the pipetter tip being slowly rotated to gather the precipitated DNA; FIG. 8D shows the precipitated DNA on the tip being dried by immersion of the tip in 70% ethanol (tip is then withdrawn for air drying); FIG. 8E shows the DNA on the tip being resuspended in a hydration solution (tip being vibrated to hasten resuspension and thus detachment of the DNA from the tip); and FIG. 8F shows primers, Taq polymerase, and water being added to prepare the DNA in the microdroplet for PCR or other downstream protocol.

SEQUENCE LISTING

Figure 1:
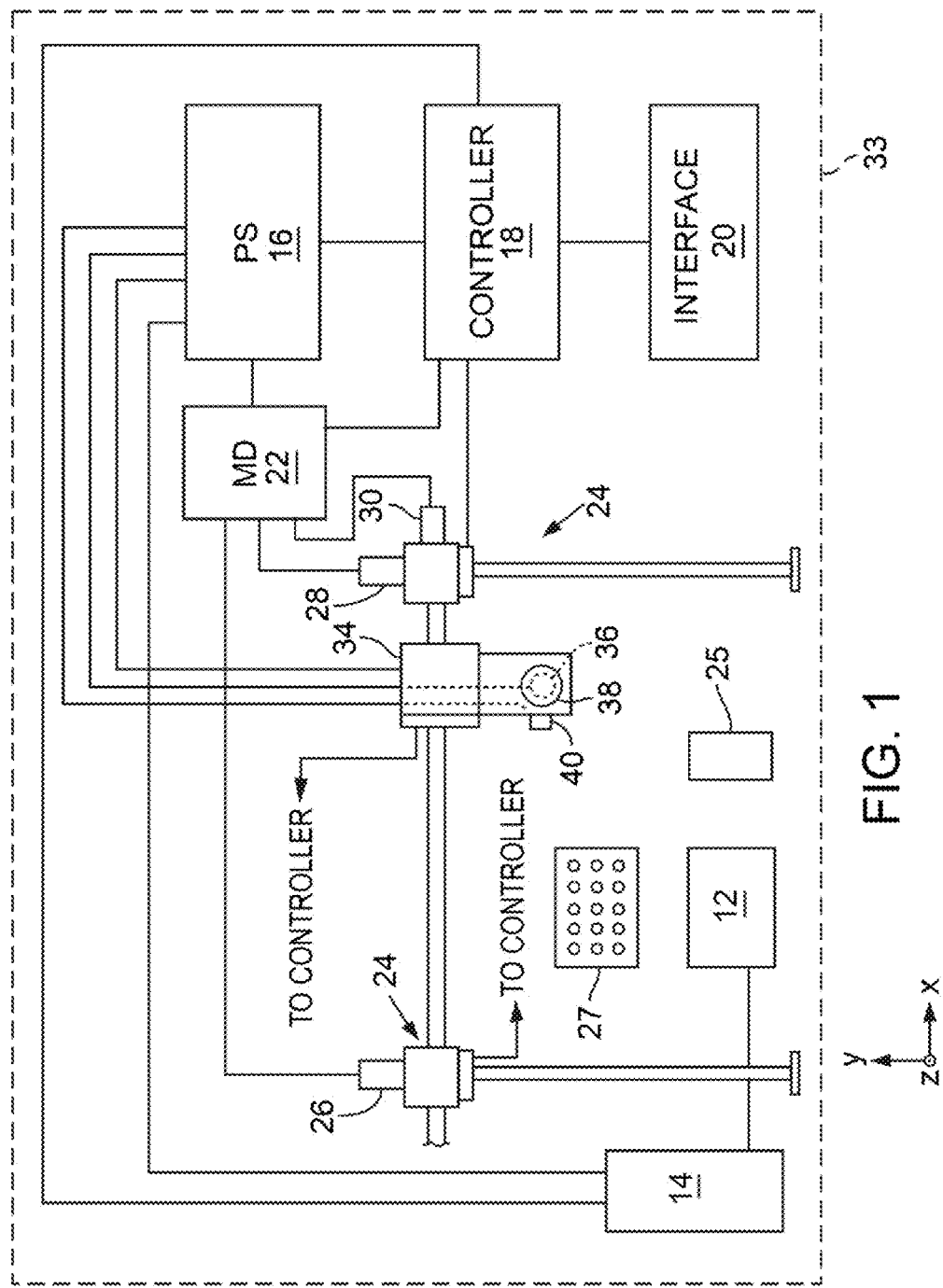
FIG. 1 is a schematic diagram of the first representative embodiment of a microdroplet-protocol system.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named SeqList-87746-01.txt, created Aug. 29, 2011, about 1.2 KB, which is incorporated by reference herein. In the accompanying sequence listing:

SEQ ID NOs: 1 and 2 are forward and reverse primers for amplification of a nucleic acid sequence of the *Escherichia coli* K12 aminoacyl-histidine dipeptidase (pepD) gene.

SEQ ID NOs: 3 and 4 are forward and reverse primers for amplification of a nucleic acid sequence of the H1N1 influenza A RNA polymerase subunit PA gene.

DETAILED DESCRIPTION

The disclosure is set forth below in the context of multiple representative embodiments, which are not intended to be limiting in any way.

The drawings are intended to illustrate the general manner of construction and are not necessarily to scale. In the detailed description and in the drawings themselves, specific illustrative examples are shown and described herein in detail. It will be understood, however, that the drawings and the detailed description are not intended to limit the invention to the particular forms disclosed, but are merely illustrative and intended to teach one of ordinary skill how to make and/or use the invention claimed herein.

As used in this application and in the claims, the singular forms "a," "an," and "the" include the plural forms unless the context clearly dictates otherwise. Additionally, the term "includes" means "comprises." Further, the term "coupled" encompasses mechanical as well as other practical ways of coupling or linking items together, and does not exclude the presence of intermediate elements between the coupled items.

The described things and methods described herein should not be construed as being limiting in any way. Instead, this disclosure is directed toward all novel and non-obvious features and aspects of the various disclosed embodiments, alone and in various combinations and subcombinations with one another. The disclosed things and methods are not limited to any specific aspect or feature or combinations thereof, nor do the disclosed things and methods require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and method. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In the following description, certain terms may be used such as "up," "down,", "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

The use of controlled mechanisms for manipulating liquid microdroplets on an open, superhydrophobic surface was previously investigated (You et al., *Faraday Discuss.* 149: 159-170, 2011, incorporated herein by reference in its entirety). Briefly, a clean metal wire was used for guiding motion of a hydrophilic-liquid microdroplet that had formed on a superhydrophobic surface. This is the source of the term "wire-guide," Yoon and You, *J. Biol. Eng.* 2:15, 2008 (incorporated herein by reference). In addition to using wires for manipulating microdroplets, also evaluated was the use of analogous structures for microdroplet manipulation (e.g., blunt hypodermic needles and pipetter tips) having any of a variety of materials, sizes, and configurations for applying different forces to liquid microdroplets. Thus, as used herein, a "wire-guide" system includes use of any of the microdroplet-manipulating devices described herein. The wire-guide system proved to be adaptable to a wide range of microdroplet volumes and properties. It was also discovered that a blunt, hollow needle or disposable pipetter tip attached to a mechanized syringe or analogous device can be vibrated or otherwise moved in a particular manner for use in precisely dividing and splitting liquid microdroplets, for mixing the contents of a microdroplet, and for rotating the microdroplet. It was also found that wire-guiding can allow protocols to be performed on, in, or with microdroplets depending from the ends of hollow needles or pipetter tips. These protocols include any of various dilution protocols and various PCR protocols, in which movement of a pendant microdroplet while submerged in an inert hydrophobic oil provides good and rapid convective transfer of heat to and from the microdroplet as required.

Polymerase Chain Reaction as an Exemplary Protocol

The Polymerase Chain Reaction (PCR) is a well-established method for detecting and amplifying DNA and RNA. PCR has unlimited sensitivity and unparalleled specificity. It is an essential tool and medical research and clinical medicine. It is used extensively for detecting infectious disease organisms and detecting gene mutations. Reverse transcription PCR (RT-PCR) is a variant of PCR in which an RNA strand is first reverse transcribed to complementary DNA (cDNA) using the enzyme reverse transcriptase. The cDNA is then amplified using traditional PCR.

PCR is an in vitro amplification technique that increases the number of copies of a nucleic acid molecule (for example, a nucleic acid molecule in a sample or specimen). In particular examples, amplification of a nucleic acid molecule of defined length is achieved by multiple cycles of a three-step procedure involving denaturing a DNA template, annealing oligonucleotide primer pairs to opposite strands of the template, and extending the primers with a thermally stable DNA polymerase to copy each strand of the template. Each step of a PCR cycle is carried out at a specific temperature. Target DNA is denatured at high temperature (such as at 95-98° C., such as about 95, 96, 97, or 98° C.). The temperature for annealing primers to complementary target DNA strands by nucleic acid hybridization is typically sequence-specific. Common primer-template annealing temperatures are between about 50-56° C., such as about 50, 51, 52, 53, 54, 55, or 56° C. Primer extension is carried out at a polymerase-specific temperature. Repeated polymerase exposure to high temperature in the denaturing step necessitates use of a thermal-stable polymerase, many of which are known in the art. In particular examples, the Taq DNA polymerase is used, and extension is carried out at about 72° C. Exemplary embodiments of systems disclosed herein are used to amplify DNA by PCR. However, one of skill in the art will recognize that the described systems can be used in other exemplary methods of DNA amplification such as isothermal amplification methods, which can use fewer than three temperature-controlled chambers of the described PCR vessel. Representative and non-limiting examples of isothermal in vitro amplification techniques include strand-displacement amplification (see U.S. Pat. No. 5,744,311); transcription-free isothermal amplification (see U.S. Pat. No. 6,033,881); repair chain-reaction amplification (see WO 90/01069); ligase chain-reaction amplification (see EP-A-320 308); gap-filling ligase chain-reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

The product of a PCR or other amplification technique can be characterized by various standard techniques known in the art, such as electrophoresis, restriction endonuclease cleavage patterns, oligonucleotide hybridization or ligation, and/or nucleic acid sequencing.

PCR and other amplification methods and techniques for characterizing amplification products are well-known in the art, and are described, for example, in Ausubel et al. (eds.), *Current Protocols in Molecular Biology*, published by Wiley InterScience, 2011 (ISSN 1934-3639). Additionally, methods for preparing and using nucleic acid primers are described, for example, in Sambrook et al. (In *Molecular Cloning: A Laboratory Manual*, CSHL, New York, 1989), and Innis et al. (*PCR Protocols, A Guide to Methods and Applications*, Academic Press, Inc., San Diego, Calif., 1990).

In particular embodiments of PCR, known as real-time or quantitative PCR, methods and devices are used for detecting and measuring products generated during each PCR cycle, which are proportionate to the amount of template nucleic acid prior to the start of PCR. The information obtained, such as an amplification curve, can in some examples be used to quantify the initial amounts of template nucleic acid sequence. In particular embodiments, real-time PCR is accomplished using nucleic acid probes that can be included in an amplification reaction, for example to permit detection of formed amplicons (such as in real time). In one example, the detectable label associated with the probe is a fluorophore. The fluorescence signal intensity can be related to the amount of PCR product (amplicon) by a product-dependent decrease of the quench of a reporter fluorophore, or by an increase of the Förster resonance energy transfer (FRET) from a donor to an acceptor fluorophore. FRET is the radiationless transfer of excitation energy by dipole-dipole interaction between fluorophores with overlapping emission and excitation spectra. Because the FRET and the quench efficiency are strongly dependent on the distance between the fluorophores, the PCR-product-dependent change in the distance between the fluorophore can be used to generate the sequence-specific signals.

Several different probes can be used in real-time PCR methods. All can function by a decrease of quench or an increase of FRET. In one example, 5' nuclease fluorogenic target-specific oligonucleotide probes are utilized. One particular example of such a probe is a TaqMan probe (Applied Biosystems, Foster City, Calif.), which includes a reporter fluorophore at the 5' end, and a quencher internally or at the 3' end. An exemplary 5' reporter fluorophore is FAM (5-carboxyfluorescein), and an exemplary 3' quencher fluorophore is TAMARA (6-carboxy-tetramethylrhodamine). Intact probes do not produce a fluorescent signal because they are quenched. In one example, during extension of the primers, the TaqMan probe, which is complementary to the amplicon sequence, is bound to the single-stranded PCR product like the primers. Upon reaching the probe, Taq DNA polymerase (due to its intrinsic nuclease activity) cuts the probe, releasing the quencher from the reporter fluorophore, which now fluoresces after excitation with the appropriate wavelength of light. The signal generated by the reporter fluorophore is detected, and quantitation of the amplicons can be made by analysis of the resulting amplification curve.

Commercial PCR systems generally utilize a single Peltier module for heating and cooling a sample-containing vial to the various temperatures required in a PCR cycle. This is a major disadvantage of conventional automated PCR systems. Among the three principal modes of heat transfer (conduction, convection, and radiation), conduction is the least efficient for heating and cooling liquid samples. Also, since most commercial PCR systems utilize only a single heating block instead of separate blocks (one for each temperature in the PCR cycle) the temperature of the single block must be changed repeatedly for use in the next thermal step. Repeatedly changing the temperature of a single heating block consumes valuable time (usually a significant portion of the total PCR cycling time) as well as power. In methods as disclosed herein, a separate respective heater is used for each temperature in the cycle, the heaters are held, as required, at constant respective temperatures, and the sample is moved from one heater to the next as it progresses through a PCR cycle. By eliminating single-block warm-up and cool-off, the PCR cycle times are substantially reduced.

An approach to reducing PCR cycling times in conventional PCR protocols is focused on reducing sample volumes. Much of this work has been directed to using of microfluidics, in which small volumes of liquid travel through microchannels. Unfortunately, these microchannel devices rely upon conductive heat transfer for heat cycling of the sample. Since conductive heat transfer is relatively inefficient and slow, several minutes are usually required to complete each cycle. This results in over an hour being required to perform typically 25-30 cycles of PCR. See, e.g., Kopp et al., *Science* 280:1046-1048, 1998.

In conventional PCR devices employing microchannels, liquid flows continuously through the microchannel, or flows within a microchannel as discrete liquid plugs. Although microchannel PCR can be performed more rapidly than certain other conventional PCR assays, a serious limitation is the lack of adaptability of the microchannel PCR device. Namely, microchannels formed in a unit of material are difficult if not impossible to reconfigure for a different protocol or change in the usual protocol. Usually, replacement of the existing microchannel piece with a new one specifically configured for the new protocol is required. Changing the protocol even slightly typically requires a redesign of the microchannel piece. Also, sample-dependent pre-processing steps such as cell lysis, DNA/RNA extraction, and/or reverse transcription (RT) are difficult to implement in a microchannel piece not specifically configured for performing these additional steps. Additionally, these conventional systems are closed systems, meaning that once a sample has been introduced as a droplet into a microchannel, the process cannot be interrupted or augmented until the droplet has completed its course or the sample has been expelled from the system.

Conventional techniques for manipulating droplets on open, flat surfaces include electrowetting-based microfluidics (Chang et al., *Biomed. Microdevices* 8:215-225, 2006) and magnetofluidics (Ohashi et al., *Biomed. Microdevices* 9:695-702, 2007). Apparatus and methods focused primarily on electrowetting on dielectrics are difficult to fabricate and to operate, and the technique has problems with diffusional mixing and contamination due to increased wetting on the surface. Magnetofluidics includes adding magnetic particles to the droplets to facilitate moving the droplets over a superhydrophobic surface using a magnet. This raises concerns of adverse effects being introduced to the samples as a result of adding magnetic particles to them, e.g., particle interference with biological or biochemical reactions.

To resolve the issues with conventional techniques as summarized above, Applicants arrived at wire-guided microdroplet microfluidics (using a microdroplet-manipulating device) as being the simplest and most efficient technique for performing various protocols with the desired speed and efficiency. No magnetic particles are required, and wire-guided microdroplet microfluidics can be implemented easily in a variety of microdroplet environments and situations. Samples having microdroplet-sized volumes (1-50 µL, such as any of 1-10, 10-20, 20-30, 30-40, and 40-50 µL, e.g., 5, 10, 15, 20, 25, 30, 35, 40, 45, 50 µL) allow for lower reaction volumes and decreased assay times for many common laboratory procedures. Using a microdroplet-manipulating device, such as a wire, syringe, pipetter tip, or the like, multiple-step protocols can be performed upon, in, and with microdroplets on or in a hydrophobic milieu, such as on open, flat, superhydrophobic surfaces or within biologically inert, hydrophobic oil or other suitable hydrophobic liquid. These protocols are easily reconfigurable at any time before, during, or after performing a particular protocol. For example, an extra step(s) can be added on the fly to an ongoing protocol, as required or desired, without having to change the system. In addition, the system can be programmed to perform multiple microdroplet-manipulation protocols, or portions thereof, in combination. A combination can include, for example, all of one protocol plus all of another, all of one and part of another, part of a first protocol and all or part of another, or multiple protocols or parts thereof. In addition, any of the microdroplet-manipulation protocols described herein can be combined with one or more thermal-cycling protocols such as PCR or a portion thereof, performed using the system as discussed later below.

Another advantage of wire-guided microfluidics is its ready utility with microdroplet volumes that are not excessively small. There are conventional "nanodrop" and related schemes in which the PCR assay is performed in very small, stationary droplets (smaller than most microdroplets). The droplet volumes are extremely small (nanoliter volumes), mostly in an attempt to speed up conduction-based heat transfer. Even though this "stationary droplet PCR" approach has allowed significant reduction in PCR thermal cycling time compared to other conventional methods, the extremely tiny volume (typically in the nanoliter range) makes it very difficult to confirm the products of the PCR thus performed (e.g., by gel electrophoresis, subsequent imaging, and/or gene sequencing). Nanodrop PCR also raises concerns of assay reproducibility and reliability. For example, dividing a low-concentration sample into nanoliter volumes may result in one or more droplets not receiving any of the target molecules. In wire-guided microfluidics, in contrast, the volume of a microdroplet can be kept sufficiently large (e.g., 1-10 µL) to allow confirmation of its products and ensuring the reliability of the assay.

Moreover, the systems described herein can be additionally configured to perform real-time PCR protocols. Such systems include means for exciting and detecting of a fluorescent probe, which are well known in the art.

First Representative Embodiment

This embodiment is directed to a microdroplet-protocol system comprising a movement and placement device. The movement and placement device in this embodiment is a computer-numerical-controlled (CNC) system ("wire-guide system") that provides controlled motion in at least two dimensions (e.g., x and y) and more desirably in three dimensions (x, y, and z).

The system of this embodiment is configured for performing various biochemical and molecular biological protocols, such as (but not limited to) microdroplet serial dilution, microdroplet centrifugation, DNA extraction from a microdroplet, and PCR (including thermocycling) of the extracted (or other) DNA. DNA extractions and microdroplet centrifugations can be performed in air (or inert gas) on a superhydrophobic surface as an exemplary hydrophobic milieu. PCR thermocycling desirably is performed under an inert hydrophobic liquid in a multi-chambered PCR vessel including multiple heaters. The system has essentially no limitations on the complexity and/or configuration of procedures that it can perform. i.e., the range of possible protocols represents any of various combinations of microdroplet-manipulation protocols and cyclic-heating protocols. Also, a user can start and/or stop at any time a protocol being performed by the system and insert a change to the protocol (including execution of one or more manual operations, if desired), followed by automatic resumption of the original protocol or another protocol.

As used herein, a "hydrophobic milieu" is an either surficial or liquid environment that favors formation of substantially spherical microdroplets of a hydrophilic liquid placed in contact with the milieu. Substantially spherical microdroplets can be manipulated in the various ways described herein. Significant deviation from sphericity tends to make a microdroplet more difficult to manipulate. A first example of a hydrophobic milieu is a superhydrophobic surface (i.e., a surface on which a microdroplet of hydrophilic liquid tends to assume a substantially spherical shape (contact angle usually 150° or more, but desirably less than 180°). Another example of a hydrophilic milieu for a microdroplet is immersion in a hydrophobic liquid, such as an inert hydrophobic oil (e.g., silicone oil). Either type of hydrophobic milieu shapes a hydrophilic droplet into a substantially spherical shape, which is important for manipulating the microdroplet. Note that "super" hydrophobicity is important for the surface but not for the liquid.

A general system configuration of this embodiment is shown in FIG. 1. The depicted system 10 resembles, in part, a computer-controlled or robotic system configure to perform various programmed tasks. In this embodiment, the system 10 is configured to perform various actions on, in, and with microdroplets. The system 10 of this embodiment comprises a PCR vessel 12, a temperature controller 14, a power supply 16, a controller or computer 18, a user interface 20, a motor driver 22, an x-y wire-guide system 24, an array 27 of pipetter tips, vials (some possibly containing reagents and/or samples as required), and a planar superhydrophobic surface 25. FIG. 1 depicts the following example electrical interconnections: The PCR vessel 12 includes multiple heated zones and temperature sensors that are connected to the temperature controller 14. The temperature controller 14 is connected to the power supply 16 and the controller 18. The user interface 20 is connected to the controller 18. The controller 18 is connected to the power supply 16. The power supply 16 is connected to the motor driver 22. The motor driver 22 is connected to stepper motors 26, 28, 30 of the x-y wire-guide system 24, to the power supply 16, and to the controller 18. The entire system 10 is mounted to a base 32 that can be placed, for example, on a laboratory bench-top. Details on these individual components are provided later below.

Referring further to FIG. 1, the x-y wire-guide system 24 of this embodiment includes a carriage 34 that rides on and is guided by guide rods while moving in the x- and y-directions. Further details of the wire-guide system 24 are provided later below in the discussion of FIG. 2. Motion of the carriage 34 in the x- and y-directions is actuated by respective stepper motors 26, 28, 30. Mounted to the carriage 34 are a syringe holder 36 or analogous device and drive motors 38 for moving the syringe holder (and thus the syringe) up and down (z-direction movement) and for moving the syringe plunger up and down (z-direction movement) relative to the syringe holder 36. Operably coupled to the syringe (particularly at or near the "tip end" of the syringe) is a vibration motor 40 used for imparting desired rapid periodic motions of the syringe end (and thus of a needle, wire, pipettor tip, or the like mounted to the syringe end). For these various motions, the controller 16 is electrically connected to the syringe holder 36, the motors 38, the vibration motor 40, and to the carriage 34.

This system 10 is configured to position a controllably actuatable syringe 36 and needle (or pipetter tip or other implement), used for manipulating microdroplets, relative to the hydrophobic milieu, such as the superhydrophobic surface 25 (on which serial dilutions and DNA extractions, for example, can be performed). The system also controls operation of the syringe and needle (or pipetter tip or other implement) for manipulating microdroplets in the PCR vessel 12 (in which PCR thermocycling, for example, can be performed).

Figure 2:
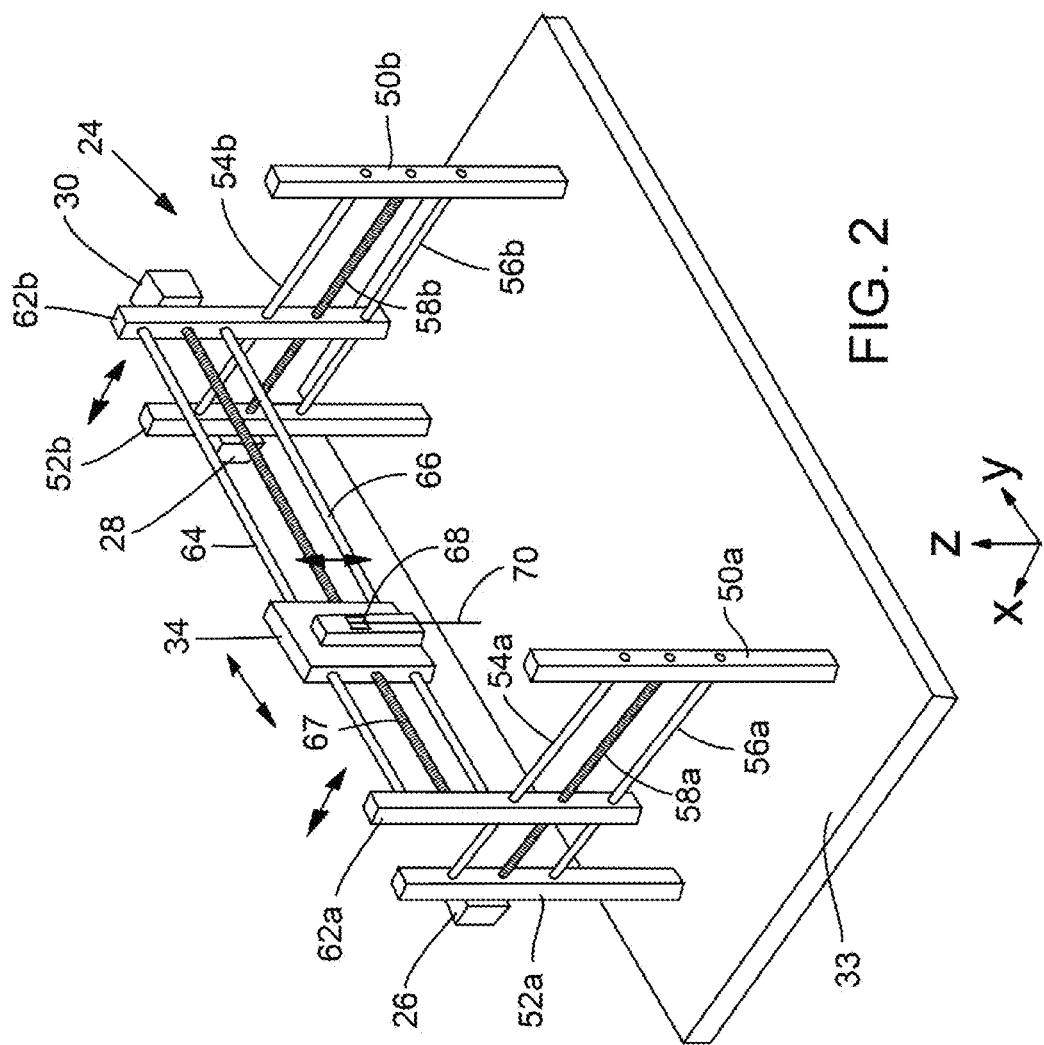
FIG. 2 is a perspective view of the x-y wire-guide system of the first representative embodiment, the system being an exemplary controlled movement and placement device having a range of movement in at least two dimensions.

The x-y wire-guide system 24 of this embodiment is shown in FIG. 2. The x-y wire-guide system 24 is an example of a "movement and placement device" because it moves and places the carriage 24, and hence the syringe, and hence a needle, tip or other implement mounted to the tip end of the syringe, at a desired location and placement to execute a respective action on a microdroplet as set forth in a protocol. The wire-guide system 24 includes support members 50a-50b and 52a-52b mounted vertically (z-direction) to the base 32. Extending in the x-direction between the support members 50a and 52a are parallel guide bars 54a, 56a, and extending in the x-direction between the support members 50b, 52b are parallel guide bars 54b, 56b. Journaled in both support members 50a, 52a parallel to the guide bars 54a, 56a is a threaded rod 58a. Similarly, journaled in both support members 50b, 52b parallel to the guide bars 54b, 56b is a threaded rod 58b. The guide bars 54a, 56a also extend through respective slide bushings (not shown) in a movable member 62a, and the guide bars 54b, 56b also extend through respective slide bushings (not shown) in a movable member 62b. The bushings (and thus the movable members 62a, 62b) move with extremely low friction along the guide bars 54a, 54b, 54b, 56b. Meanwhile, the threaded rod 58a is threaded through a ball screw (not shown) mounted in the movable member 62a so that axial rotation of the threaded rod 58a causes linear movement of the movable member 62a in the x-direction. Similarly, the threaded rod 58b is threaded through a ball screw (not shown) in the movable member 62b so that axial rotation of the threaded rod 58b causes linear movement of the movable member 62*b* in the x-direction. Simultaneous rotation of the threaded rods 58*a*, 58*b* is achieved by respective stepper motors 26, 28 simultaneously rotating at identical angular velocities as controlled by the motor driver 22. Spanning between the movable members 62*a*, 62*b* and the y-direction are parallel guide bars 64, 66. The guide bars 64, 66 extend through respective slide bushings (not shown) in the carriage 34. The bushings (and thus the carriage 34) move with extremely low friction along the guide bars 64, 66. Meanwhile, a threaded rod is journaled in the movable members 62*a*, 62*b* parallel to the guide bars 64, 66. The threaded rod 67 is threaded through a ball screw (not shown) in the carriage 34 so that axial rotation of the threaded rod 67 causes movement of the carriage 34 in the y-direction. Rotation of the threaded rod 67 is caused by a respective stepper motor 30 controlled by the motor driver 22.

The particular configuration of the wire-guide system 24 described above is one example of a mechanical structure capable of providing controlled movement and placement of the syringe or other implement relative to microdroplets on or within a hydrophobic milieu, such as on a superhydrophobic surface or in an inert hydrophobic oil. Any of various other x-y-z manipulator structures can alternatively be employed to provide the same motions as the wire-guide system 24. It will also be understood that the guide bars, threaded rods, and ball screws can be replaced with analogous mechanisms such as, but not limited to, linear motors and analogous devices, or belt-driven mechanisms.

As noted, mounted to the carriage 34 is a syringe holder 36 operably coupled to the motor 38 for raising and lowering the syringe 68 in the z-direction. The motor 38 is connected to and controlled by the motor driver 22. Also, a vibration motor 40 is mounted to the carriage 34 and coupled to the syringe 68 (or at least to the tip-end of the syringe) to impart, as needed, a circular or otherwise suitable vibratory motion to the syringe tip as the syringe is being held by the syringe holder 36. Yet another actuator (not shown) mounted to the carriage 34 is a linear actuator that controllably moves the syringe plunger (not detailed) in the z-direction to enable the syringe to aspirate or release a microdroplet of liquid, for example.

The combinations of x-, y-, and z-motions of the syringe 68 produced by the wire-guided system 24 allows a needle, pin, pipette tip, or other suitable tool 70 attached to the syringe to be placed anywhere in three-dimensional space defined by the wire-guide system 24. Motions of the motors 26, 28, 30, 38, 40 are achieved using respective motor-control circuits provided in the motor driver 22 as controlled by the controller 18 and powered by the power supply 16. Since a stepper motor operates by a train of electrical pulses that can be counted by the respective motor-control circuit, there is usually no need for a device, such as a linear or rotary encoder, that monitors position of either the movable members 62*a*, 62*b* or the carriage 34.

The syringe 68 can be of a disposable nature for convenience. It will be understood that the term "syringe" is not limited to conventional clinical syringes but rather encompasses various implements having the ability to aspirate, release, and/or manipulate liquid microdroplets in the conditions prevailing in the system 10. These implements include pipetters and the like that typically use disposable tips, as used widely used in biochemistry and molecular biology. The term "syringe" also encompasses various devices that are analogous to syringes and pipetters. Use of a clinical syringe 68 as the implement is not limited only to syringes to which conventional hollow needles are attached. Certain types of syringes may utilize, for example, disposable pipetter tips instead of needles. Thus, for microdroplet insertion and extraction, a syringe 68 mounted to the syringe holder 36 can be fitted with a disposable pipetter tip or a modified conventional (e.g., Luer-Lok™) blunt-ended needle or other suitable tool. As noted, the syringe holder 36 includes at least one linear actuator 38 that drives the syringe plunger in the z-direction as required and moves the syringe 68 up and down, as required, relative to the carriage 34. Also, as noted previously, a vibration motor 40 causes rapid periodic motion of the syringe and/or its needle as described later below. In addition, the syringe can be provided with yet another actuator that provides controlled motion of the syringe (or at least a tip fitted thereto) around the z-axis (as used in, e.g., collecting precipitated DNA on the syringe needle or pipetter tip during execution of the DNA extraction protocol.

Therefore, the syringe 68 as an exemplary tool is not intended to be limiting in any way. Substantially any implement or tool useful for microdroplet manipulations can be mounted to the carriage 34. No matter which implement is used, the system 10 provides x-y-z motion of the implement to any location reachable by the carriage 34 riding on the guide rods and lead screws.

It will also be understood that more than one implement can be mounted to the carriage 34; additional drive mechanisms can be added to the carriage 34 to provide independent manipulation (including motion relative to the carriage 34) of multiple implements mounted to the carriage. Alternatively, each of multiple carriages can include respective implements that are independently movable relative to their respective carriages.

Furthermore, although a clean, metal wire was initially used to guide an aqueous microdroplet on the superhydrophobic surface, the wire can be replaced with any of a variety of microdroplet-manipulating devices of various materials and sizes to modulate the force of the microdroplet to the wire ($W_a$), making the system 10 highly adaptable to a wide range of microdroplet volumes and properties. Syringe needles or disposable pipetter tips have ready utility for use in, for example, precise splitting and mixing of microdroplets as aided by actuation of the vibration motor 34 and the motor moving the syringe plunger relative to the syringe itself.

This embodiment is particularly well suited for performing PCR thermocycling and for performing auxiliary protocols such as, but not limited to, serial dilution of a sample, concentration of a sample by centrifugation, and DNA extraction, all being preparatory to performing PCR. For example, an exemplary process performed by the system 10 can begin with serial dilutions of a sample (e.g., 10-fold serial dilutions). Following dilution, the system 10 can concentrate a sample microdroplet by "centrifugation" achieved by spinning the microdroplet in situ at a high angular velocity using the syringe needle actuated by the vibration motor 40. During centrifugation, the more dilute portions of the microdroplet at the axis of rotation can be is drawn into the syringe, leaving the more concentrated portion of the sample for further analysis. The sample can then be subjected to DNA extraction, in which a wire-guided needle performs extraction, separation, and removal of the precipitated genetic material. Afterward, the system 10 can amplify a particular genetic sequence(s) in the sample by PCR thermocycling or analogous technique. The results of the amplification can be confirmed by gel electrophoresis or other suitable method.

Most tasks other than PCR cycling can be performed on the open, flat superhydrophobic surface 25. PCR cycling is not suitable for performance on the superhydrophobic surface 25 because the high temperatures involved in PCR thermocycling can evaporate very quickly a sample exposed to air. Consequently, PCR thermocycling desirably is performed in the PCR vessel 12. The hydrophobic milieu is provided by submersion in a suitable (i.e., hydrophobic and chemically inert) oil that maintains the microdroplets as spherical entities amenable to manipulation, that prevents sample evaporation, and speeds up thermocycling.

Thus, microdroplet manipulations take place on or in a hydrophobic milieu. As discussed previously, a hydrophobic milieu can be a surface or substance (e.g., liquid) that, when contacted by a hydrophilic (e.g., aqueous) liquid, tends to form the hydrophilic liquid into substantially spherical microdroplet(s). Spherical microdroplets of the hydrophilic liquid are important for performing any of various manipulations on, in, or with the microdroplets. In particular examples, the hydrophobic milieu is a superhydrophobic surface. In other examples the hydrophobic milieu is a hydrophobic, inert liquid, such as silicone oil. The superhydrophobic surface 25 is essentially an open, flat (planar) substrate (e.g., a glass substrate) having a surficial treatment or inherent property in which the upper surface thereof is provided with a superhydrophobic property. In this embodiment, the superhydrophobic surface used a commercial product having planar dimensions of 25×55 mm, although this is not limiting in any way. In general, a "hydrophobic" surface exhibits contact angles, with aqueous microdroplets (e.g., microdroplets of water, buffered solution, and the like) on the surface, of greater than 90°. For example, a smooth, glass surface coated with a film of alkylsilane or Teflon™ exhibits a contact angle to aqueous microdroplets of approximately 110°, and hence is a hydrophobic surface. But, a simply hydrophobic surface does not provide sufficiently high contact angles with which to perform certain microdroplet manipulations, such as centrifugation, on the superhydrophobic surface. A "superhydrophobic" surface is one on which the contact angle of an aqueous microdroplet is in the range of approximately 150° to 180°. In this range, contact angles of approximately 150-155° are optimal for microdroplet manipulations on the superhydrophobic surface. A droplet having a contact angle greater than approximately 155° may be manipulatable with the systems described herein, but may also exhibit difficulty in remaining on the superhydrophobic surface. Achieving superhydrophobicity is not limited to application of a superhydrophobic substance to the surface. Other ways of achieving super hydrophobicity include, but are not limited to, surface roughening to increase the effective unit area of the surface (Wenzel, *Ind. Eng. Chem.* 28:988, 1936; and Wenzel, *J. Phys. Colloid Chem.* 53:1466, 1949), or treating the surface to form an array of micron or submicron sized asperities with hollows between them to provide two different contact angles, according to the Cassie model (Cassie and Baxter, *Trans. Faraday Soc.* 40:546-551, 1944; Cassie, *Discuss. Faraday Soc.* 3:11-15, 1948).

The PCR vessel 12 provides an array of multiple respective temperature zones ("chambers") in which the respective temperature steps in the PCR protocol are performed on a microdroplet. The PCR vessel 12 is also configured to contain hydrophobic oil in which the aqueous microdroplet can be immersed to prevent evaporation of the microdroplet and to accelerate heating of the microdroplet. The microdroplet typically remains in the oil throughout the entire time the microdroplet is in the PCR vessel 12, including during transport from one chamber thereof to the next. For most PCR protocols, the PCR vessel comprises three chambers. However, this is not limiting, and the PCR vessel can have, for example, greater or fewer than three chambers for greater flexibility and/or as required. One of skill will appreciate that the "PCR vessel" is not limited solely for the purpose of performing PCR reactions. Rather the "PCR vessel" can be used in any protocol requiring one or more multiple temperature stages and which could result in microdroplet evaporation if otherwise performed in air. Moreover, any one of the chambers can be used independently in any application or procedure that requires a temperature-controlled environment produced by a heat block, water bath, and the like.

Figure 3A:
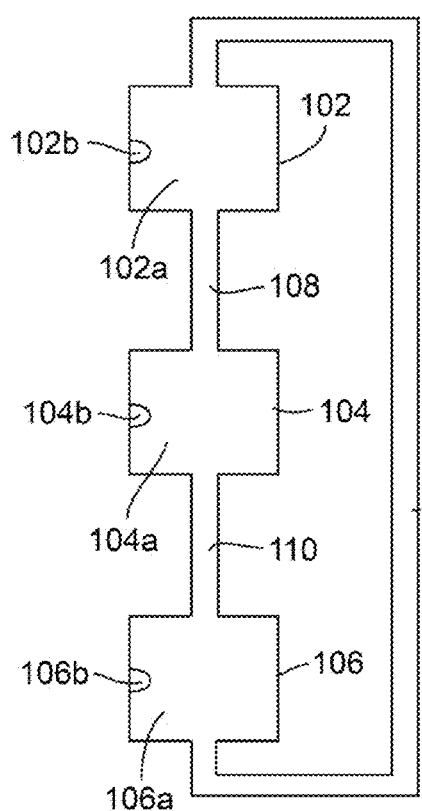
FIG. 3A is a plan view of a first example PCR vessel comprising three respective chambers arranged substantially linearly.

Whereas PCR reactions are performed using the system 10, several different configurations of multi-chamber PCR vessels were considered. The first configuration 100 had three temperature zones ("chambers") 102, 104, 106 connected in line, as shown in FIG. 3A. Each chamber 102, 104, 106 included its own heater 102a, 104a, 106a and its own temperature sensor 102b, 104b, 106b. The chambers 102 and 104 were connected by a channel 108, and the chambers 104 and 106 were connected by a channel 110. The chambers 106 and 102 were also connected by a channel 112. The chambers 102, 104, and 106 and channels 108, 110, and 112 were all open on top. A sample microdroplet being subjected to PCR thermal cycling was passed, using a needle or pipetter tip attached to the syringe, sequentially through the first chamber 102, the channel 108, the second chamber 104, the channel 110, the channel 106, and the channel 112 to return to the chamber 102 to repeat the cycle. The in-line PCR vessel 100 worked fine for PCR thermocycling, and each chamber 102, 104, and 106 maintained its respective temperature even though the chambers were connected together by the channels 108, 110, and 112. However, the non-cyclic arrangement of the chambers required an unnecessarily long travel of the microdroplet (via the channel 112) at the end of each cycle as the microdroplet returned from the third chamber 106 to the first chamber 102.

Figure 3B:
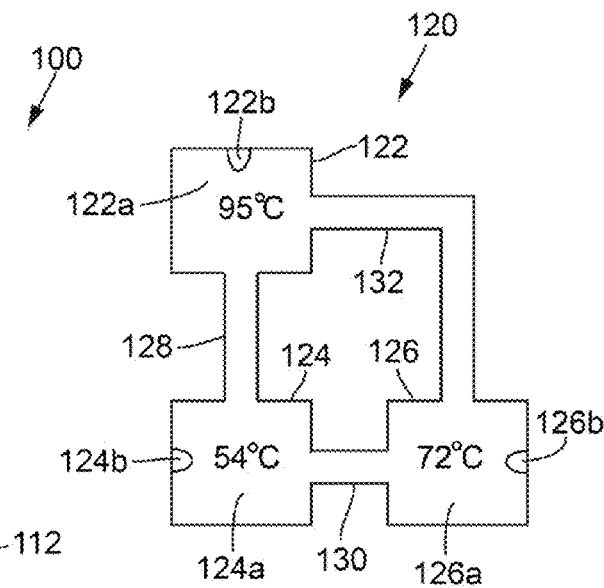
FIG. 3B is a plan view of a second example of PCR vessel comprising three respective chambers configured in a two-dimensional arrangement.

Therefore, a more cyclic arrangement 120 of chambers 122, 124, and 126 was considered a more desirable arrangement (e.g., the arrangement shown in FIG. 3B), in which the channel 132 is substantially shorter than the channel 112 in FIG. 3A. In FIG. 3B, the chambers 122, 124, and 126 correspond to the chambers 102, 104, and 106, respectively, in FIG. 3A. Similarly, the channels 128, 130, and 132 correspond to the channels 108, 110, and 112 in FIG. 3A. (See also FIG. 3C.) At the bottom of each chamber 122, 124, and 126 is a respective heater 122a, 124a, and 126a that is independently controlled to maintain a respective temperature in the respective chamber. To such end, each chamber includes a respective temperature sensor 122b, 124b, and 126b. The heaters and sensors are connected to the temperature controller 14 (FIG. 1). The PCR vessel 120 is made of ABS polymer, for example, although any of a large variety of inert, rigid, heat-tolerant, and oil-tolerant materials could alternatively be used, including many plastics and metals, and certain glasses and ceramics. The rectilinear (square) profile of the chambers as shown is not limiting. Square chambers correlate to the shape of the particular heaters selected for use in this embodiment. By changing the shape of the heaters, the chambers could be made in any shape. For example, the chambers could be hexagonally shaped or circularly shaped to shorten the intervening channels or to eliminate them entirely. (However, the channels may be useful for thermal isolation of the chambers from each other.) In the particular embodiment shown in FIGS. 3B and 3C, the respective heater of each chamber was configured as exposed copper traces on a single-cited printed circuit board, and the temperature sensor was a thermocouple. Other types of heaters and temperature sensors can alternatively be used.

In particular examples, the PCR vessel 120 can include a real-time monitoring circuit that is connected to means for exciting and detecting an excited fluorophore in the PCR reaction microdroplet. Exemplary means includes a photodiode that could be situated adjacent a channel connecting together two chambers in the PCR vessel 132 (see second representative embodiment). The photodiode is situated to receive light from a laser diode or the like disposed on the opposite side of the channel, and the photodiode and laser diode together can be used to monitor the progress of a PCR reaction as the microdroplet moves between the diodes in the channel. (If the microdroplet passes through the channel while retracted in the needle or pipetter tip, the needle or pipetter tip should be transmissive to the wavelength(s) of light produced by the laser diode.) The monitoring circuit monitors amplified products produced by real-time PCR and other protocols performed in the PCR vessel. The monitoring circuit is connected to a user interface to display the results of the monitoring of the PCR reaction.

Figure 3C:
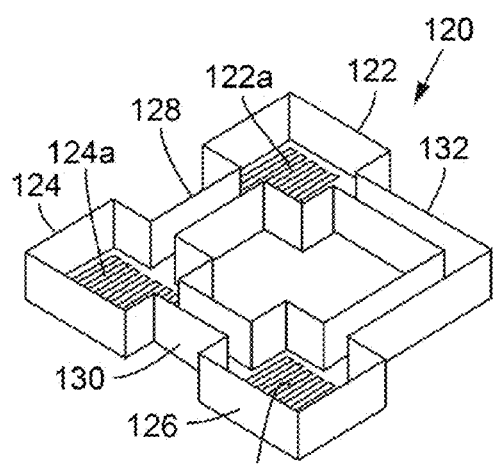
FIG. 3C is a perspective view of the PCR vessel shown in FIG. 3B.

With the PCR vessel 120 shown in FIGS. 3B and 3C, steady-states for the three necessary PCR cycling temperatures (for example, about 95° C., about 54° C., and about 72° C. in the chambers 122, 124, and 126, respectively) were achieved in a compact, connected configuration. In this exemplary embodiment, actual oil temperatures were set to 105° C., 55° C. and 80° C., respectively, to ensure rapid heating of a microdroplet in a very short time and to compensate for thermal losses from the chambers and channels.

Temperature variations parallel to the heater 122a, 124a, and 126a in any chamber 122, 124, and 126 did not vary more than ±1° C. except near the respective walls of the chamber. The depth of the temperature sensor (thermocouple) resulted in a more significant temperature variation of ±2° C. Thus, the depth of the sensor 122b, 124b, and 126b relative to the depth of the microdroplet in each chamber was considered to ensure proper heating of the microdroplet in the chamber.

During normal use, the PCR vessel 120 contains the inert hydrophobic oil in which the microdroplet(s) is submerged during execution of PCR thermocycling (or any other incubation procedure). The oil desirably is chemically inert, of relatively low viscosity, stable to the temperatures encountered in the PCR vessel, and does not contribute any substance to the microdroplet. For this purpose, silicone oil is particularly desirable, but any other oil or hydrophobic liquid meeting these criteria will suffice.

Figure 4:
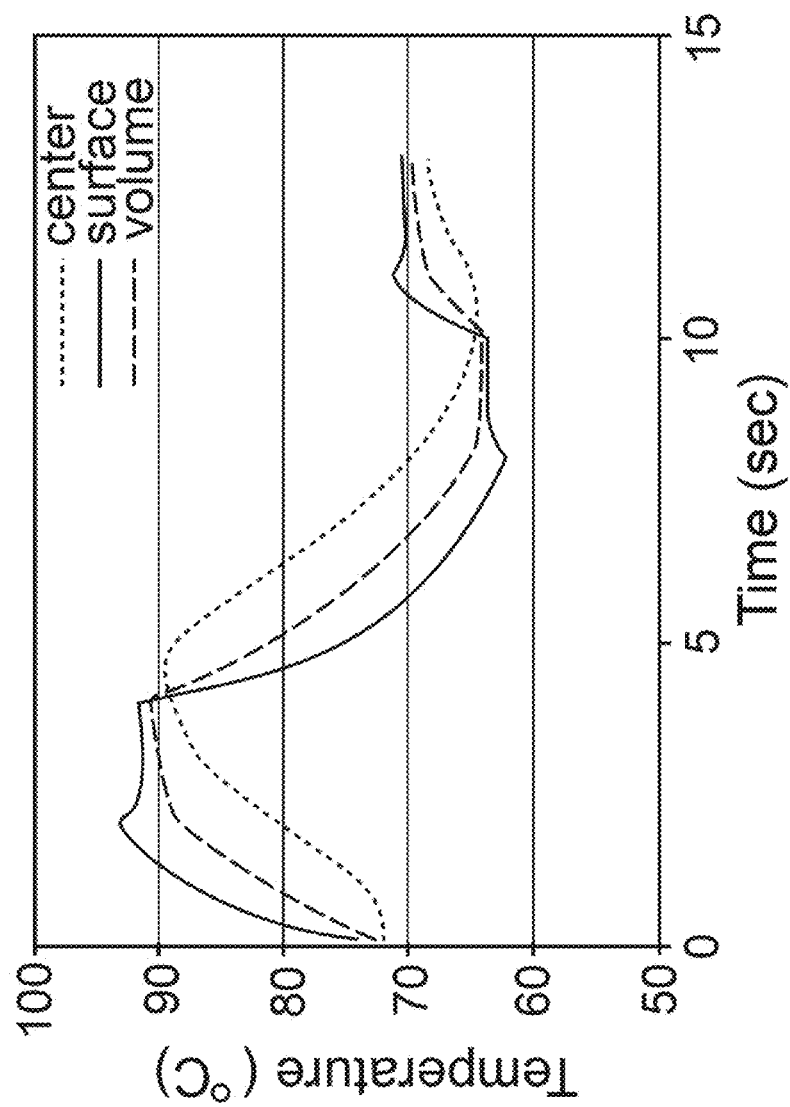
FIG. 4 is a plot of temperature versus time as obtained in a CFD simulation showing that a single PCR cycle performed with a 10 µL microdroplet can be completed in 13 seconds with the microdroplet remaining for two seconds in each chamber of the PCR vessel (typical extension rate=80 nucleotides per second, with a 2-second holding time required per step for a 160 bp amplification), indicating that a 30-cycle PCR can be completed in six minutes 30 seconds.

CFD modeling was performed on a microdroplet as it traveled in silicone oil through the three chambers of the PCR vessel. The parameters of the simulation were; a 10 µL microdroplet traveling at a rate of 2 cm/s through uniformly heated silicone oil. The simulation revealed the effects of convective heat transfer on the microdroplet at its surface and throughout its volume. Data obtained from the simulation of convective heat transfer to the microdroplet were data-logged and used to plot a graph of temperature versus time (FIG. 4). The plot shows the temperature of the microdroplet at its center, on its surface, and throughout its overall volume. Heating of the microdroplet from 72° C. to 95° C. occurred in approximately 2 seconds in the 95° chamber 122 (actual temperature 105° C.), cooling from 95° C. to 62° C. occurred in approximately 4 seconds in the 54° C. chamber 124 (actual temperature 55° C.), and heating from 62° C. to 72° C. occurred in approximately 1 second in the 72° C. chamber 126 (actual temperature 80° C.).

Therefore, the overall time consumed in heating and cooling a 10-µL microdroplet for one PCR cycle is theoretically seven seconds. However, because particles will accumulate primarily at the oil-to-water interface of the microdroplet, these times may be significantly reduced. If the microdroplet is additionally maintained at the correct temperature for two seconds per chamber, then the overall PCR cycle takes approximately 13 seconds. With these times, performing 30 cycles of PCR of a 10-µL microdroplet would only require six minutes 30 seconds. Use of a smaller microdroplet size may further shorten the PCR time.

Microdroplets of 10 µL size were selected for use because such volumes closely match the volumes used in typical PCR assays. Also, 10 µL provides sufficient volume for further analysis to be conducted on the sample, such as gel electrophoresis and/or DNA sequencing. (Without performing these post-analysis procedures, the product of a PCR protocol may not be definitively determined or may lead to unreliable conclusions.) The range of microdroplet size usable with the system 10 is governed principally by the range of microdroplet size that can be manipulated, particularly on the superhydrophobic surface. Microdroplets that are too large collapse on the surface and hence lose the roughly spherical shape desired for manipulation. Microdroplets that are too small evaporate too quickly, even on the superhydrophobic surface. Hence, a practical range is about 1 µL to 50-100 µL, such as about 1-10 µL, about 10-20 µL, about 20-30 µL, about 30-40 µL, about 40-50 µL, about 50-60 µL, about 60-70 µL, about 70-80 µL, about 80-90 µL or about 90-100 µL.

Microdroplet manipulation in the PCR vessel 120 was performed using a hollow blunt needle fitted to the syringe 68, with the needle pointing downward. While in a particular chamber of the vessel 120, the microdroplet can remain hanging (i.e., pendant) from the blunt tip of the needle or pipetter tip to facilitate convective heat transfer from the oil to the microdroplet or vice versa. Keeping the microdroplet pendant is readily achieved because the microdroplet only needs to stay in a given chamber for four to five seconds. The microdroplet can also remain pendant when traveling from one chamber to the next if the velocity of this travel is sufficiently low. Within each chamber 122, 124, and 126 of the PCR vessel 120, the velocity of the controlled movements of the syringe 68 was set to 2 cm/s, and this same velocity can be used when transporting the microdroplet from one chamber to the next. If the velocity of inter-chamber transfer is increased (above 2 cm/s), then the resultant force of oil on the pendant microdroplet may cause the microdroplet to detach and fall from the needle. To achieve faster PCR cycle times while preventing detachment of the microdroplet from the needle, the microdroplet can be retracted up into the needle by backing the syringe plunger slightly, prior to commencing inter-chamber movement of the microdroplet. Then, when the needle arrives in the next chamber, the syringe plunger can be moved to push the microdroplet back out of the needle (while keeping the microdroplet pendant from the needle). This action, including microdroplet retraction during inter-chamber movement, significantly reduces the time needed for PCR thermocycling.

The motor (e.g., a linear stepping motor) used for moving the syringe plunger relative to the syringe 68 was calibrated to insert and retract exactly a 10 µL aqueous microdroplet into each chamber of the PCR vessel. The microdroplet was pushed completely out of the syringe needle (while remaining pendant) in each chamber. Conductive heat loss or gain between the needle and microdroplet was considered; but, since the microdroplet was pendant, the contact area of the microdroplet with the needle tip, relative to the contact area of the microdroplet to the surrounding oil, was quite small. Also, since the microdroplet and syringe needle move together and remain in direct contact with each other, the method of heat transfer between the two is conduction. Heat transfer between the microdroplet and the oil, on the other hand, is primarily convection, which provides a much higher rate of heat transfer. Therefore, Applicants concluded that the effects of the needle on the thermocycling temperatures in the chambers of the PCR vessel were minimal.

Microdroplet Insertion and Extraction

For insertions and extractions of microdroplets, a disposable syringe can be used that is fitted with a disposable pipetter tip or a blunt-ended hypodermic needle, for example. An exemplary syringe size is a disposable 1-mL plastic syringe, but a syringe of any volume capacity that can fit into the syringe holder 36 can be used. For such a syringe, the syringe holder 36 can be a quick-release type that holds the syringe parallel to the z-axis of the system with the needle pointing downward. The syringe plunger is actuated (by a motor, piezoelectric stack, or the like) to move the plunger in either z-axis direction relative to the syringe.

Serial Dilution

The apparatus 10 can readily perform serial dilutions of a sample containing any of various analytes of interest. The analyte can be living (e.g., bacterial cells or plant cells or animal cells) or inanimate (e.g., DNA or RNA). Serial dilutions desirably and conveniently are performed in microdroplets on the superhydrophobic surface 25, although they alternatively can be performed in microdroplets under oil in the PCR vessel. Serial dilutions are performed using the syringe 68, the movements of which are largely produced and guided by the x-y wire-guide system 24 or other controlled movement and positioning device.

Figure 5A:
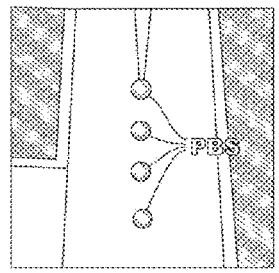
FIGS. 5A-5H are a series of images of a serial-dilution protocol performed using the first representative embodiment. In the protocol a guided pipetter tip manipulates, splits, and mixes the contents of discrete microdroplets situated on a superhydrophobic surface as an example of a hydrophobic milieu.
Figure 5B:
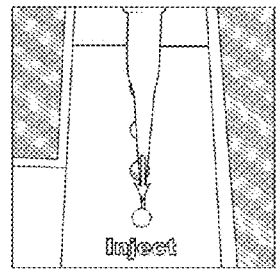
Figure 5C:
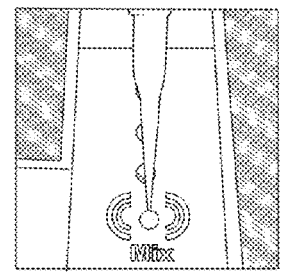
Figure 5D:
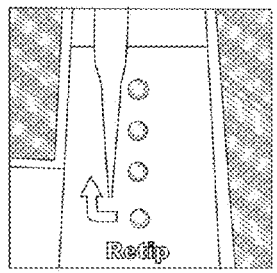
Figure 5E:
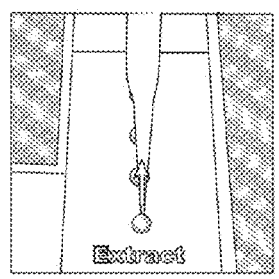
Figure 5F:
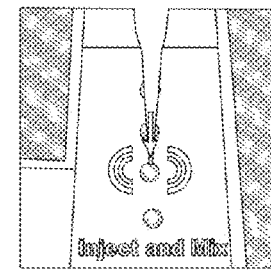
Figure 5G:
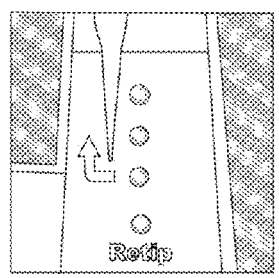
Figure 5H:
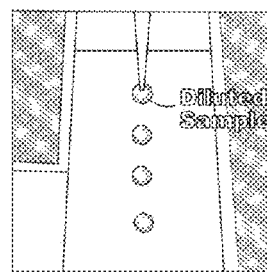

The sequence of events of sample dilution, including serial dilution, is shown in FIGS. 5A-5H; see also Example 1. Using the syringe 68 fitted with a disposable pipetter tip or needle, an array of microdroplets of diluent is placed on the superhydrophobic surface (FIG. 5A). An exemplary microdroplet volume is 20 µL. A predetermined volume of sample (e.g., 2 µL) is added to the first microdroplet (FIG. 5B). The first microdroplet is then mixed (FIG. 5C) by keeping the distal end of the needle or pipetter tip immersed in the microdroplet and agitating the syringe using the vibration motor 40. The syringe is retipped (FIG. 5D) by moving the syringe 68 to the rack 27 where the used needle or pipette tip is discarded and a fresh one attached to the syringe (automatically by executing appropriate motions of the syringe). During this moment, the system may automatically re-calibrate itself to insure precision of subsequent actions. The syringe is moved back to the superhydrophobic surface to remove an aliquot (e.g., 2 µL) from the first microdroplet and add the aliquot into the second microdroplet (FIG. 5E). The second microdroplet is then mixed (FIG. 5F) in the same manner as the first microdroplet, followed by retipping the syringe (FIG. 5G) as previously. These steps are repeated (FIG. 5H) for each remaining microdroplet of diluent in the array on the superhydrophobic surface.

Clearing the superhydrophobic surface for its next use is as simple as either aspirating the microdroplet(s) using the syringe as a pipette and then discarding the pipette tip, or simply guiding the microdroplet off the surface into a tissue in which the microdroplet is absorbed and later discarded. Further alternatively, the superhydrophobic surface can simply be replaced (e.g., with a sterile one).

Microdroplet Centrifugation

The system disclosed herein performs concentration of a diluted sample by microdroplet "centrifugation," as controlled by a controlled movement and placement device. For such action, the syringe is fitted with a blunt-ended tip or needle, and the tip is inserted into a microdroplet (resting on the superhydrophobic surface) containing a substance to be separated from the carrier liquid of the microdroplet. Hence, this is an in situ centrifugation technique. The needle tip is inserted into the microdroplet, and the needle is actuated by the vibration motor to vibrate in two dimensions while immersed in the microdroplet. The resulting spinning of the microdroplet tends to concentrate the substance in outer regions of the microdroplet relative to the center of the microdroplet. In this embodiment the vibration motor 40 is operated by a pulse-width-modulated (PWM) algorithm to generate the most favorable 2-dimensional motion path (e.g., oval or circular), which can be verified by high-speed imaging. To maximize the number of rotations per minute (RPM), the PWM algorithm was executed to isolate a resonant frequency that induced the most stable and rapid 2-D path (e.g., elliptical or substantially circular) of the needle in the microdroplet. RPMs of over 2000 have resulted in useful analyte concentration. RPMs of 10,000 or more are readily producible.

One of ordinary skill in the art will appreciate that the frequency of motion of the needle may change between samples due to variations from one sample to the next of needle height from the superhydrophobic surface, changes in contact angle of the microdroplet to the superhydrophobic surface due to variations in microdroplet content, and/or changes in the connection between the needle and the syringe. In such event, requisite small changes can be made to the PWM frequency using the user interface 20. Example frequencies, not intending to be limiting, range from approximately 1000 rpm to 10,000 rpm or more.

Figure 6A:
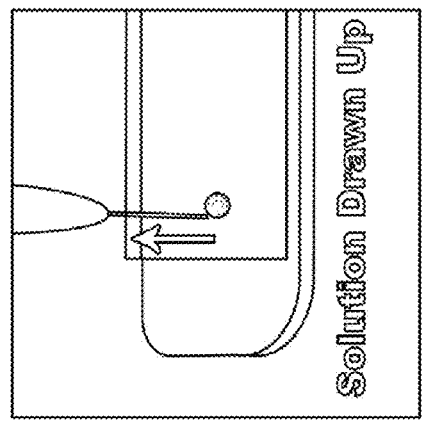
FIGS. 6A-6E are a series of images of a protocol for concentrating a sample by droplet centrifugation performed on the superhydrophobic surface.
Figure 6B:
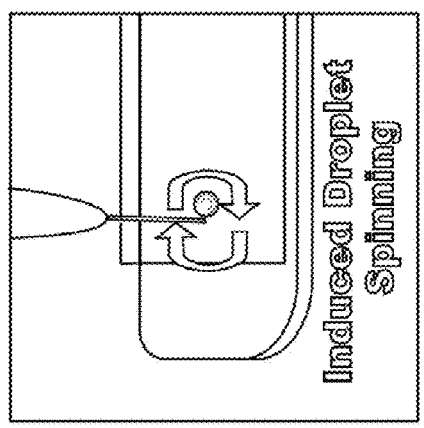
Figure 6C:
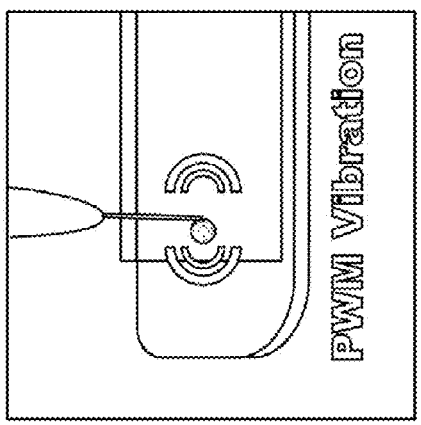
Figure 6D:
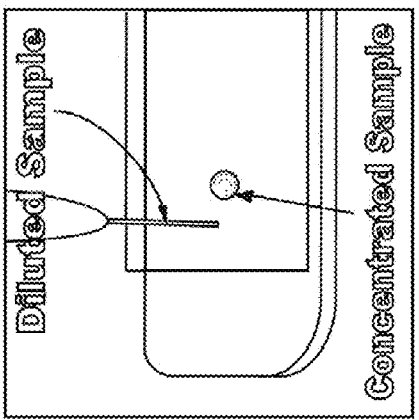
Figure 6E:
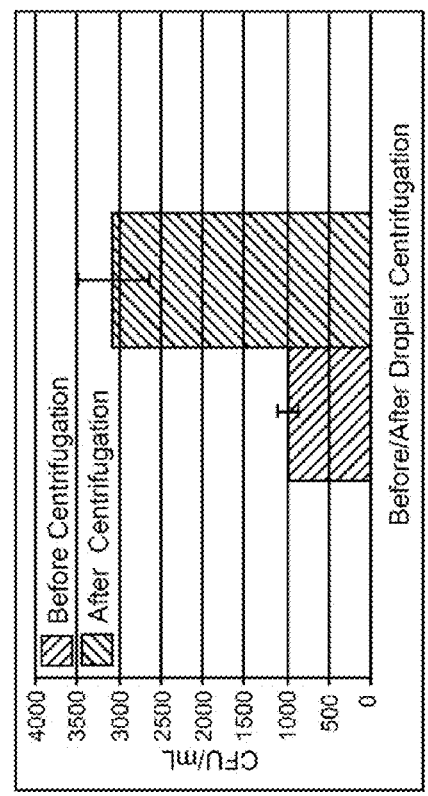

Centrifugation of a microdroplet is illustrated in FIGS. 6A-6E, involving a microdroplet containing bacterial cells. FIG. 6A depicts the syringe needle undergoing PWM vibration. Also shown is the microdroplet resting on the superhydrophobic surface. FIG. 6B shows the needle tip inserted in the microdroplet and causing the microdroplet to spin as a result of the vibration imparted to the syringe needle. In an example, the microdroplet is caused to spin at approximately 2000 RPM, which produces a centrifugation force of 22×g. FIG. 6C shows the needle aspirating sample-poor liquid from the center of the microdroplet after concluding spinning. FIG. 6D shows the needle being withdrawn from the remaining microdroplet of concentrated sample. FIG. 6E is a bar graph showing the concentration of bacteria in a 10-µL sample before and after microdroplet centrifugation, wherein a three-minute centrifugation produced a 3.06-fold increase in mean concentration of bacterial cells.

In FIG. 6C, after a specific period of centrifugation, the syringe extracts liquid from the center of the microdroplet. This extraction can be done at a slower rate (e.g., ~0.5 µL/s) compared to sample dispensation, to reduce potential turbulence induced by the aspiration and subsequent decrease in microdroplet diameter.

Extraction and Amplification of Genetic Material

The system of this embodiment also performs extraction and amplification of genetic material from living cells using the same apparatus configuration and on the same superhydrophobic surface as the procedures described above. The only difference is the execution of a different preprogrammed algorithm for extraction and amplification of genetic material, compared to the other procedures.

Rapid DNA extraction from a concentrated sample is illustrated in FIGS. 7A-7H and GA-GF. In FIG. 7A a microdroplet of concentrated sample (containing living cells) is placed on the superhydrophobic surface. In FIG. 7B a cell-lysis solution is added to the microdroplet using the syringe fitted with a pipetter tip. In FIG. 7C, the syringe aspirates the microdroplet from the superhydrophobic surface and moves the drop to a lysis chamber heated to 80° C. The lysis chamber can be either one of the chambers of the PCR vessel, notably the nominally 72° C. chamber (actual temperature is 80° C.) 126 or a separate chamber. If the lysis chamber is a separate chamber, the lysis chamber can be constructed similarly to one of the chambers of the PCR vessel in that it includes a heater and a temperature sensor. The lysis chamber also includes a volume of an inert hydrophobic oil, such as silicone oil, in which the microdroplet can be submerged during this step. In FIG. 7D the microdroplet now containing lysed cells is returned, using the syringe, from the lysis chamber to the superhydrophobic surface. In FIG. 7E, isopropyl alcohol solution is added to the microdroplet to precipitate the DNA in the microdroplet. Particularly if the pipetter tip is plastic, the DNA adheres to the tip. This collection can be facilitated by slowly rotating the tip by slow "centrifugation" using the vibration motor 40. In particular examples, wherein the precipitating DNA does not adhere to the pipette or other "wire guide" tip, precipitating DNA can be concentrated and recovered by the microdroplet centrifuging method described above. In FIG. 7F the pipetter tip (with attached DNA) is washed in 70% ethanol. In FIG. 7G the syringe is retracted and the DNA on the surface of the pipetter tip is allowed to air dry. In FIG. 7H the syringe tip is lowered into a microdroplet of hydration solution on the superhydrophobic surface to resuspend the DNA in the solution. To hasten resuspension of the DNA, the syringe needle may be vibrated using the vibration motor 40.

The steps described above are also shown in FIGS. 8A-8F. The protocol shown in FIGS. 8A-8F is particularly directed to preparing a sample for PCR. In FIG. 8A a microdroplet of concentrated sample of *E. coli* (from a microdroplet-centrifugation procedure) is placed on the superhydrophobic surface. In FIG. 8B cell-lysis solution is added to the microdroplet and mixed there with by vibrating the syringe needle. The microdroplet is then transferred to and heated in the lysis chamber at 80° C. for three minutes. In FIG. 8C, after completion of cell lysis, the microdroplet is removed from the lysis chamber, and isopropanol is added to precipitate the DNA. While slowly rotating the needle tip, the precipitated DNA adheres to the tip. In FIG. 8D, the precipitated DNA is washed in 70% ethanol, and the syringe tip is removed from the microdroplet for air drying. In FIG. 8E, after air-drying the DNA is resuspended in hydration solution, as aided by vibration of the needle as required. In FIG. 8F, the microdroplet is prepared for PCR.

An innovative step in the DNA-extraction procedures discussed above is the one in which the precipitated DNA is conveniently extracted from the microdroplet using the syringe tip as a substrate. Since the microdroplet is resting on the superhydrophobic surface, the predominant force is the electrostatic interaction of the genetic material toward the pipetter tip during removal, making the extraction process fast and easy with minimal residual fluid needing to be evaporated.

Polymerase Chain Reaction

Using the described system 10, any PCR protocol can be conducted on a sample immediately following extraction of DNA therefrom or at any other time when a DNA- or RNA-containing sample is available for analysis.

For performing PCR, a PCR vessel, such as the PCR vessel described in FIGS. 3B and 3C is utilized. The PCR vessel contains a volume of silicone or other inert hydrophobic oil in which the microdroplets are manipulated and heated at each step of the PCR cycle. The PCR process is essentially a thermocycling process that occurs over three different temperatures: denaturation at 94-96° C., annealing at 50-65° C., and extension at 72° C. Each stage in the cycle occurs in a separate chamber of the PCR vessel, beginning with denaturation. A syringe needle tip or pipette tip is used to control the movement of the microdroplet while the microdroplet is submerged in oil during each stage, and is used to transfer the microdroplet from one chamber to the next. During the time the microdroplet is in a chamber, the microdroplet is pendant from the tip of the needle, and the needle continuously moves the microdroplet relative to the oil in the chamber to ensure good convective heat transfer from the oil to the microdroplet (or vice versa). During transfer from one chamber to the next, the microdroplet desirably is retracted into the tip and pushed back out after it has entered the next chamber. An exemplary PCR procedure involves 30 cycles. After PCR, the sample can be analyzed using a technique such as gel electrophoresis.

In addition to PCR, the system can also perform related techniques that require multiple temperature incubation steps, such as reverse transcriptase PCR (RT-PCR). During PCR, the Taq DNA polymerase, or any other thermally stable DNA polymerase, can be used to amplify the DNA sequence of interest. Typical extension rates of the polymerase utilized thus far are about 80 nucleotides per second. Thus, for a template 160 nucleotides or less, about two seconds of holding time at each temperature of the cycle is usually needed for each step of the cycle, for a total of six seconds per cycle. In addition, about two seconds are required at each step for heating up or cooling down the microdroplet, with the exception of the initial denaturation step that takes about three seconds, yielding a total of about seven seconds. Therefore, a single cycle of PCR can be completed within 13 seconds for a 10-µL microdroplet. If a smaller microdroplet is used, e.g., 1 µL, the heating/cooling time can be reduced to less than one second each, allowing a single cycle of PCR to be completed in as few as six seconds. Therefore, using any of the embodiments disclosed herein, a 20-cycle PCR amplification of a 160-bp gene can be completed in just two minutes. One of ordinary skill will appreciate that, for nucleic acid templates that are longer or shorter than 160 base pairs, incubation time can be adjusted accordingly to enable complete copying of the nucleic acid sequence of interest. Similarly, incubation times can also be adjusted to account for variations in polymerization rates of different thermal stable DNA polymerases.

Second Representative Embodiment

Figure 9:
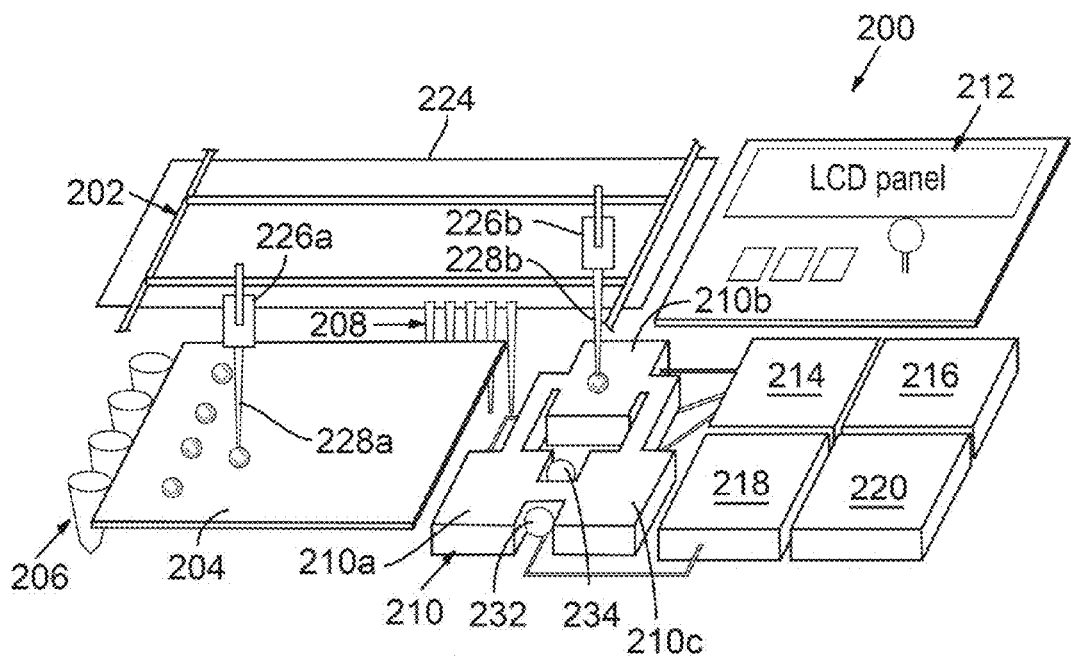
FIG. 9 is a perspective view showing a general layout of components of a microdroplet manipulation system according to the second representative embodiment.

This embodiment of a microdroplet-protocol system is illustrated in FIG. 9. The system is directed to a hand-held system 200 similar in many ways to the first representative embodiment 10, but substantially reduced in size. Similar to the first representative embodiment 10, the second representative embodiment 200 performs the entire PCR process, as well other thermal processes performable under oil, and various processes performable on the superhydrophobic surface. These processes include, but are not limited to, serial dilution, centrifugation, DNA extraction, sample incubation (such as for reverse transcription), and thermocycling for PCR, all being performed on, in, or with microdroplets.

A schematic diagram of this embodiment 200 is shown in FIG. 9, and includes a three-axis CNC manipulator (an exemplary controlled movement and placement device) 202, a superhydrophobic surface 204, a rack 206 of vials, a rack 208 of pipetter tips and/or needles, a PCR vessel 210 comprising at least three chambers 210a, 210b, 210c, a user interface 212, a heating circuit 214, a microcontroller 216, a real-time monitoring circuit 218, and a rechargeable battery 220. At least the racks 206, 208, PCR vessel 210, controlled movement and placement device 202, and superhydrophobic surface 204 are sequestered from the external environment, but are visible to a user, through an overlying window 224. The system 200 is hand-held or usable on a work surface.

The user may choose a pre-programmed protocol that is stored within the microcontroller 216, or may create his/her own protocol using the user interface 212. To such end, the user interface 212 comprises requisite buttons, icons, user-prompts, joystick, or other data-entry means. Also if desired, the user can interrupt an ongoing process at substantially any time during the process, enter a modification to the process, and then resume the process or restart the process.

Since the system is battery-operated and has its own user interface 212 and its own microcontroller, there is no need for an external computer to enable use of the system except for upgrading the software in the microcontroller. Pipetter tips (or syringe needles or other tools) are used to withdraw microdroplets of sample/reagent from a vial in the rack 206, to transfer the microdroplet(s) to the superhydrophobic surface 204, and to manipulate individual microdroplets on the superhydrophobic surface (for serial dilution/centrifuging/DNA extraction, for example). Pipetter tips and/or needles are also used for delivering microdroplets to and moving the microdroplets in the PCR vessel 210. By observing through the window 224, the user can monitor microdroplet manipulations and interrupt and reprogram as needed. Pipette tips are typically used only once and discarded. The rack 206 of vials, rack 208 of pipetter tips, the superhydrophobic surface 204, and the PCR vessel 210 collectively can be made as a single disposable cartridge for use with only a single set of samples.

In this and other embodiments, the controlled movement and positioning device provides a simple manner in which microdroplets are manipulated, compared to a conventional system. Manipulations of the microdroplet can be performed on an open surface or under oil using a wire or needle, wherein the needle is either solid or hollow, or any of various pipetter tips and the like. These tools can be selected with respect to materials, sizes, and configurations thereof relative to the size, shape, volume, and density of the microdroplets, thereby making the system highly adaptable to a wide range of microdroplet volumes and properties. Furthermore, the use of a syringe needle or disposable pipetter tip can be used to perform precise microdroplet splitting, mixing, diluting, as well as microdroplet centrifugation, by appropriately moving and/or vibrating the tool.

The controlled movement and positioning device 202 in this embodiment may include a first carriage 226a and a second carriage 226b, both being positionable as commanded by the microcontroller 216 in the three-dimensional space encompassed by the controlled movement and positioning device. Mounted to the first carriage 226a is a first syringe 228a, and mounted to the second carriage 226b is a second syringe 228b. Providing multiple syringes allows the system 200 to perform correspondingly multiple protocols simultaneously or correspondingly different steps of a particular protocol simultaneously, as commanded by the microcontroller 216.

This embodiment includes a real-time monitoring circuit 220 that is connected to a photodiode 232 situated adjacent a channel connecting together two chambers in the PCR vessel 210. The photodiode 232 is situated to receive light from a laser diode 234 or the like disposed on the opposite side of the channel. The monitoring circuit monitors amplified products produced by PCR and other protocols performed in the PCR vessel 210. The photodiode 232 desirably is an avalanche photodiode. The voltage signal from the photodiode is conditioned and amplified using an analog op-amp circuit, converted to digital signal using an open source microcontroller board such as Arduino, and the integrated signal is displayed on a small liquid crystal display that is connected to a microcontroller board. This feature provides real-time quantification of the PCR process. Depending upon the outcome of the real-time quantification, the user can interrupt the PCR protocol at any time and restart the protocol using a different or modified protocol.

This and other embodiments, such as the first representative embodiment, can be used in a wide variety of applications, including but not limited to, detecting and quantifying infectious agents in various settings, medical diagnostics, veterinary diagnostics, environmental monitoring, and general food safety. A list of potential users is as follows: (1) research laboratories (microbiology, food science, veterinary medicine, medicine, pharmacy, public health, biological/biomedical engineering, environmental science/engineering, etc.); (2) food industry (fresh produce, dairy products, meats, etc.); (3) hospital laboratories (disease diagnostics); (4) veterinary diagnostic laboratories; (5) environmental monitoring firms (e.g., air quality and water quality); (6) defense industry (e.g., biological warfare); and government agencies (e.g., NIH, EPA, CDC, USDA, DOD, etc.).

Example 1—Serial Dilution of a Bacterial Culture in a Microdroplet

This example was directed to controlled serial dilution of a concentrated sample of *E. coli* culture (in LB broth) in respective microdroplets on the superhydrophobic surface.

The serial dilution was performed in a respective array of microdroplets of diluent (e.g., phosphate-buffered saline or "PBS") placed on the superhydrophobic surface, as described above (see FIGS. 5A-5H). The volume of each microdroplet was 20 µL, and the volume transferred from one microdroplet to the next was 2 µL. Four dilutions were performed, yielding a final $10^{-4}$ dilution of the original suspension. Before performing each dilution, the syringe was moved to a location at which the syringe tip could (and was) replaced. The accuracy and precision by which the system performed the serial dilutions were evaluated using standard plate-counting methods for *E. coli*.

The standard plate-count revealed low variance in the final *E. coli* concentrations obtained after performing multiple serial dilutions.

Example 2—Microdroplet Centrifugation on a Superhydrophobic Surface

In this example, selected diluted samples of suspended *E. coli* cells were concentrated by microdroplet centrifugation. Microdroplet centrifugations were performed using a 22-gauge blunt-ended syringe needle. The vibration motor 40 executed a useful vibration of the needle by pulse-width-modulation (PWM). Each microdroplet was centrifuged in this manner for five minutes, at which point the liquid in the center of the microdroplet was aspirated therefrom using the syringe, leaving the concentrated (outer) portion of the microdroplet. Standard colony plate-counting methods were used to determine the concentrations of *E. coli* in the respective samples before and after centrifugation.

A high-speed video camera was used to obtain video images of microdroplet rotation about the syringe needle at 480 frames per second. The microdroplet rotated at 2,300 round per minute (rpm), which can further be increased by optimizing the needle size, type of vibration motor and the pulse-width-modulation (PWM).

The effects of evaporation on sample concentrations (not yet microdroplet-centrifuged) and on extracted DNA samples were also evaluated. Three case studies were compared by measuring the DNA concentration: (1) stock concentration, (2) concentration after leaving the microdroplet stationary on the superhydrophobic surface for five minutes, and (3) concentration after stifling the microdroplet for five minutes by wire-guided microdroplet centrifugation.

FIGS. 6A-6E depict the sequence of events of controlled centrifugation. The microdroplet to be centrifuged was from a liquid culture of *E. coli*. The respective concentrations of *E. coli* in the microdroplet before and after centrifugation were analyzed using standard plate-counting methods. As shown in FIG. 6E, microdroplet centrifugation produced a 3.06-fold increase in mean *E. coli* concentration after only three minutes.

Computational fluid dynamic (CFD) simulations allowed analysis of the movements of *E. coli* cells (as particles) in the microdroplets using cells of varying sizes (1, 2, 5, 7, 10 µm diameter) and their locations (as measured from the bottom of the microdroplet) versus time. When cell diameter was 5, 7, or 10 µm, 120, 60, and 30 seconds, respectively, were required for the cells to settle to the bottom of the respective microdroplet. Particles having diameters of 1 and 2 µm never reached the bottom of the microdroplet even after 300 seconds; however, they did move by ~100 µm and ~300 µm, respectively.

These results show that the system can centrifuge *E. coli* cells in a microdroplet in a short period of time. The simulation results also indicated that longer periods of centrifugation for single colonies may be sufficient for complete centrifugation.

Example 3—DNA Extraction from *E. Coli* in a Microdroplet

This example was directed to controlled DNA extraction from cells suspended in microdroplets. DNA was extracted from *E. coli* cells that were cultured in Luria-Bertani (LB) broth overnight at room temperature to prevent cells from reaching death phase. Cells were collected either by conventional centrifugation or by controlled in situ centrifugation of a microdroplet containing suspended cells, as described in Example 2.

Following concentration of the *E. coli* samples, DNA extractions were performed in the microdroplets. Nuclei-lysis solution (e.g., Promega's Cell Lysis Solution Part #A793A included in Wizard® Genomic DNA Purification Kit) was added to the microdroplets. After mixing, the droplets were heated at the 80° C. PCR chamber for 5 min. The resulting lysed samples were redeposited as microdroplets onto the superhydrophobic surface and allowed to cool. The DNA in each microdroplet on the surface was precipitated by addition of 70% isopropanol solution. After an initial mixing, the pipetter tip was rotated slowly to allow precipitated DNA to adhere to the tip. The syringe was then moved to allow air-drying of the tip for 1 min. The tip was then washed in 70% ethanol and air dried again for 1 min. Finally, the tip was immersed in DNA rehydration solution for 3 min.

Example 4—PCR Thermocycling in a Microdroplet

This example was directed to controlled PCR thermocycling of DNA obtained from bacterial cells (see, e.g., Example 3) and suspended in a microdroplet. Control PCR was performed using a conventional PCR thermocycler to ensure proper design of primers and to serve as a positive control. PCR was run according to manufacturer's instructions from the GoTaq Green Master Mix (Promega Bio-Tek, Madison, Wis.). Once positive results were verified, the controlled movement and placement device was used to detect the presence of *E. coli* DNA in the microdroplet.

An AccessQuick® PCR system kit was used for PCR performed using the controlled movement and placement device. A mixture of 4 µL GoTaq Green®, PCR reaction mix, 1 µL of each 10 µM forward and reverse primers, 1 µL of DNA sample, and 3 µL of autoclaved water, for a total of 10 µL per microdroplet. The microdroplets were subjected to 30 PCR cycles using the PCR vessel described in the First Representative Embodiment. Following DNA extraction, the system automatically attached a 14-gauge blunt-ended syringe needle (modified for friction fit) onto the syringe (by moving the syringe to the rack containing needles and lowering the syringe onto the needle). The syringe was then used to extract the PCR-ready solution (DNA solution+Taq solution+primers). The system was programmed to heat the denaturing, annealing and extension chambers of the PCR vessel to 105° C., 55° C., and 80° C., respectively. The microdroplet began the cycles in the 105° C. chamber for denaturing for 3 seconds, then the 55° C. chamber for annealing of primers for 3 seconds, and then the 80° C. chamber for extension of the products for 5 seconds. The very first denaturation was conducted for 15 seconds. The final step consisted of a final annealing for 20 seconds. As described elsewhere herein, during each of these stages, the system moved the microdroplet in a circular motion in the oil in the respective chamber to enhance convective heat transfer from the oil to the droplet. The chambers were connected together with narrow channels, which allowed the syringe needle to stay submerged in the silicone oil while moving from one chamber to the next, and preventing the possibility of microdroplet loss or evaporation due to the effects of surface tension that otherwise would arise from inserting and removing the needle from the oil each time the microdroplet was transferred to the next chamber.

To design the primers for PCR, nucleotide sequences of aminoacyl-histidine dipeptidase (pepD) and 16S ribosomal RNA from *Escherichia coli* K12 were pooled from GenBank. These sequences were then subjected to multiple alignment analysis using ClustalX to search for a conserved region so that consensus primers could be designed. Selected primers were then analyzed for appropriate melting temperature as well as any possible hairpin or self-dimerization by using OligoAnalyzer 3.1 (IDT Corporation, Coralville, Iowa, USA). Primers for pepD were 4F (5'-GGG AAT TCG TCG ACG TGT CTG AAC TGT CTC AAT T-3'; SEQ ID NO: 1) and 4R (5'-GAG CCG AAG CTT TTA CTT CGC CGG AAT TTC TT-3'; SEQ ID NO: 2) which resulted in an amplicon of about 1500 base pairs.

Figure 11:
FIG. 11 is an image of a gel in which PCR results as described in Example 4 are shown.

Gel-electrophoresis results of the PCR are shown in FIG. 11. Lane 1 shows positive control DNA extracted with culture media. The first lane is the ladder and confirms the ~1500-bp sequence being amplified. Lane 2 shows positive-control DNA extracted without culture media. Since culture media does not interfere with DNA extraction, Lane 3 shows positive control DNA from a centrifuged microdroplet. (Pelletizing the E. coli with microdroplet certification was not possible; therefore the culture media could not be completely removed). Therefore, the extent of DNA amplification was qualitatively determined by the positive controls and lanes 2 and 3, showing that there is a minimal reduction in band intensity resulting from a lower concentration of the amplified sequence. However, the strong positive band of lane 2 shows that microdroplet PCR amplification in the presence of culture media remains a viable option. Lane 4 is the result of the controlled microdroplet dilution, centrifugation, extraction, and amplification of E. coli cultured in LB media. Lane 4 exhibits an increase in signal intensity because of the PCR band achieved through effective sample concentration by controlled in situ microdroplet centrifugation. Lane 5 is the result using the identical processes that produced lane 4, less the concentrating step from microdroplet centrifugation. The band intensity of lane 4 was much stronger than that of lane 5, further indicating that microdroplet centrifugation is a useful method for concentrating samples in the interest of either increasing the positive signal of PCR amplification or reducing the number of cycles required for a positive result, thereby decreasing assay time.

Due to the long genetic sequence being amplified (~1500 bp), and corresponding extension time of 10 minutes overall (4 seconds for denaturation, 4 seconds for annealing and 8 seconds of extension, with an initial denaturation of 30 seconds and a final annealing of 60 seconds) was required to perform 30 amplification cycles.

Example 5—Modeling of Microdroplet Behavior During Controlled Centrifugation

This example is directed to CFD modeling of events associated with microdroplet centrifugation using the controlled movement and placement device. In order to track E. coli particles inside the microdroplet and to estimate the appropriate time for microdroplet centrifugation prior to DNA extraction, the commercial software (FLUENT 6.3 and GAMBIT 1.3; FLUENT Inc., Lebanon, N.H., USA) was used to build mathematical grids using the finite volume method (FVM). A 2-D model was used in this study rather than a 3-D model as the system was symmetric in shape. It was also assumed that *E. coli* particles were generated and migratory at a face parallel to the direction of gravity due to centrifugation and perpendicular to the axis of rotation.

The grid size used in the simulation consisted of 70642 cells, 106277 faces and 35636 nodes. The shape of all meshes was triangular. First-order schemes were used because they provided better convergence of calculations than the second-order, although they provided less accurate results due to the increased error in numerical discretization. An unsteady-state solution was used in order to track the movement of the *E. coli* cells by time. Since the force of gravity from centrifugation was the dominant force of interest inside the microdroplet, neither the energy equation nor turbulent model options were chosen in FLUENT. Instead, a discrete phase model was used to track the *E. coli* cells particles. It was assumed that size of the microdroplet was 4 mm in diameter. The boundary was divided evenly into four zones by distance from the bottom of the microdroplet (zone 1; 2-3 mm from the bottom, zone 2; 1-2 mm from the bottom, zone 3; 0-1 mm from the bottom). Different gravitational forces were applied to each zone (zone 1: 58.86 $m/s^2$, zone 2: 107.91 $m/s^2$, zone 3: 215.82 $m/s^2$) based on the distance of that zone from the axis of rotation. For the migratory simulation, it was assumed that the *E. coli* particles started from the top of zone 1 and migrated toward the bottom. Five cases of simulations were conducted by changing the size of *E. coli* cell (diameter of 1, 2, 5, 7, 10 μm) to simulate colony formation. Each *E. coli* cell was assumed to be a solid sphere with density of 1.2 $g/cm^3$. The time required for each *E. coli* colony to migrate to the bottom of the microdroplet was estimated for each case.

Example 6—Detection of H1N1 Influenza A by PCR

In this example pendant microdroplets, being held on the ends of blunt syringe needles were heated as required for rapid PCR thermocycling, using the PCR vessel and automated aspects of the controlled movement and placement device, as described elsewhere herein. Droplet heating was by forced convective heat transfer achieved by moving the microdroplets, while pendant and while submerged in the oil in the respective chamber of the PCR vessel, relative to the oil. In this example a 160-bp gene from influenza A/H1N1/2009 was amplified by the system in 30 cycles of PCR in 6 minutes, 50 seconds in a 10 μL microdroplet.

RNA polymerase subunit (PA) nucleotide sequences of H1N1 influenza A virus of human origin, swine origin, and avian origin were pooled from GenBank. These RNA sequences were subjected to multiple alignment analysis using ClustalX to search for conserved regions among the three different species so that consensus primers could be designed. Selected primers were analyzed for appropriate melting temperature as well as any possible hairpin or self-dimerization by using OligoAnalyzer 3.1 (IDT Corp., Coralville, Iowa). The primers designed to detect RNA polymerase subunit PA were: PAh1n1_583F (5'-CAGTC-CGAAAGAGGCGAAG-3'; SEQ ID NO: 3) and PAh1n1_745R (5'-GAAAGCTTGCCCTCAATGCAG-3'; SEQ ID NO: 4), resulting in a product of about 160 base pairs (bp).

For RNA extraction, NATtrol influenza A H1N1 virus external round control from Zeptometrix Corporation (Buffalo, N.Y.) in medium was used as a target. This virus sample is 209 H1N1flu virus of human origin, as purified/modified by the manufacturer. Its RNA was extracted using the E.Z.N.A. viral RNA kit (Promega Corp., Madison, Wis.) through a spin-column protocol. Briefly, 500 μL of QVL lysis buffer was mixed with 150 μL cell medium, then precipitated with absolute ethanol. The mixture was passed through a spin column and cleaned with RWB buffer provided with the kit. Finally, RNA was eluted from the column using elution buffer. The resulting RNA was then subjected to one-step RT-PCR.

Reverse transcription PCR (RT-PCR) was first performed using a conventional PCR machine to ensure proper design of primers and proper extraction of the RNA. RT-PCR was run according to recommendations regarding the AccessQuick™ RT-PCR system (Promega Corp., Madison, Wis.). After positive results were verified, the controlled movement and placement device was employed to detect the presence of influenza A H1N1 virus in several samples.

The AccessQuick™ RT-PCR system kit was used for the PCR reactions performed by the controlled movement and placement device. Ten-μL microdroplets were subjected to 30 cycles of PCR. After initial aspiration of the PCR solution into the syringe, the system transferred the microdroplet to a 37° C. chamber containing silicone oil for four minutes for reverse transcription to occur. After forming the cDNA template, the chamber was heated to 54° C. while the sample was undergoing an initial 30-second denaturation step performed in the 95° C. chamber of the PCR vessel. The microdroplet began each cycle in the 95° C. chamber for denaturation for 3 seconds, then transferred to the 54° C. chamber for annealing of primers for 3 seconds, and then moved to the 72° C. chamber for extension of the products for 5 seconds. The very first denaturation was conducted for 15 seconds. The final step after 30 cycles was a final annealing for 20 seconds. During each of these cycles and steps, the controlled movement and placement device moved the pendant microdroplet in a circular motion in the oil in the respective chamber to achieve good convective heat transfer to or from the microdroplet as required. The chambers were connected together with respective narrow channels to allow the syringe needle to remain submerged in the silicone oil, thereby preventing the possibility of microdroplet evaporation or loss due to the effects of surface tension arising from insertion and removal of the needle from the oil. During passage through a channel, the microdroplet was retracted into the needle.

PCR products were determined by gel electrophoresis and fluorescent imaging of the gel. The PCR products were applied to 2% low-melting agarose gel. The gel was electrophoresed using an 80-V, 1-A power supply for 60 minutes in 1× Tris-EDTA (TE) buffer solution. The gel was soaked in ethidium bromide (~1 μg/mL) for approximately 6 minutes and imaged using a GelDoc 1000 imaging system (Bio-Rad Laboratories, Hercules, Calif.).

For DNA preparation and sequencing, PCR products from a conventional PCR machine and from the controlled microdroplet system were cleaned using a QIAquck PCR purification kit (Qiagen, Valencia, Calif.) for sequencing to insure proper detection of the influenza A H1N1 virus. Amplified PCR products were sequenced using the Applied Biosystems 3730 DNA analyzer (Carlsbad, Calif.). Sequences were viewed and corrected using a Chromos Lite V 2.01 (Technelysium Pty Ltd, Southport, Queensland, Australia) and finally checked against the GenBank database.

Figure 10:
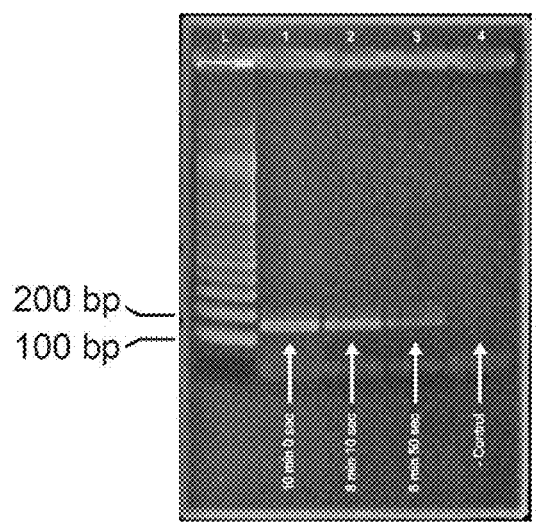
FIG. 10 is an image of a gel in which RT-PCR results as described in Example 6 are shown.

The primers used for virus detection were specifically designed to work across human, swine, and avian strains of influenza A H1N1. FIG. 10 shows a gel image of about 160 bp products of influenza A H1N1 (human origin), after 30 cycles of PCR performed in 6 minutes 50 seconds (lane 3), with an additional four-minute reverse transcription step. This minimal reverse transcription time was determined through a series of PCR experiments. Additionally, the results of 30 cycles of PCR performed in 8 minutes 10 seconds (lane 2) and in 10 minutes (lane 1) are also shown. For the results shown in lane 2 (8 minutes and 10 seconds total cycling time), the microdrop stayed in the denaturation chamber for 3 seconds, annealing chamber for 4 seconds, and extension chamber for 7 seconds, with 15 seconds initial denaturation and 30 seconds final annealing. For the results shown in lane 1 (10 minutes total cycling time), the microdrop stayed in the denaturation chamber for 4 seconds, annealing chamber for 4 seconds, and extension chamber for 6 seconds, with 15 seconds initial denaturation and 30 seconds final annealing. Lane 4 is the result of a negative control experiment in which PCR cycling was performed under the same conditions but without primers.

FIG. 10 showed that slightly less PCR amplification occurred when the 8-minute, 10-second PCR was reduced to 6 minutes 50 seconds. However, the signal from the longer-cycle experiment was still relatively strong and was considered a positive result compared to the negative control. Longer thermocycling correlated to brighter gel bands, suggesting that sufficient time is important for the Taq polymerase to amplify the DNA. If there were more DNA in the target sample or if the reverse transcription time were increased, then 20 PCR cycles may have been sufficient, which would require only (13 second)×(20 cycles)=4 min, 20 seconds to complete. Also, if a smaller microdroplet were used, e.g. 1 μL, then the time for each PCR cycle could be further reduced, making possible a 20-cycle PCR regiment performed in less than three minutes.

Although the PCR products are at the correct band size (FIG. 10), further verification was performed to validate the content of the band. PCR products were cleaned and submitted for sequencing. The genomic content of each band is then compared against the nucleotide collection database on the National Center for Biotechnology Information. The query sequence was 99% to 100% homology to various samples of 2009 H1N1 influenza A virus with an E-value of $3\times10^{-50}$ (Table 1), suggesting that the controlled movement and placement device worked properly and successfully detected this virus (99 to 100% homology) in 10 minutes or less.

TABLE 1

Comparison of amplified viral sequences to H1N1 genomic database

| Access No. | Influenza A Description | Max Score | Total Score | Query Cover | E-Value | Max Ident |
|---|---|---|---|---|---|---|
| CY056121.1A/ | Dist. Columbia/1NS31/2009(H1N1) | 219 | 219 | 95% | $3.00 \times 10^{-54}$ | 100% |
| CY053282.1A/ | Brownsville/39H/2009(H1N1) | 219 | 219 | 95% | $3.00 \times 10^{-54}$ | 100% |
| CY044906.1A/ | New York/3611/2009 (H1N1) | 219 | 219 | 95% | $3.00 \times 10^{-54}$ | 100% |
| CY050026.1A/ | Mexico City/WR1307N/2009 (H1N1) | 215 | 215 | 96% | $4.00 \times 10^{-53}$ | 99% |
| CY061804.1A/ | swine/Hong Kong/189/2101 (H1N1) | 213 | 213 | 95% | $2.00 \times 10^{-52}$ | 99% |
| CY062323.1A/ | swine/Thailand/CU-RA9/2009(H1N1) | 213 | 213 | 95% | $2.00 \times 10^{-52}$ | 99% |
| CY062255.1A/ | California/VRDL86/2009 (H1N1) | 213 | 213 | 95% | $2.00 \times 10^{-52}$ | 99% |

TABLE 1-continued

Comparison of amplified viral sequences to H1N1 genomic database

| Access No. | Influenza A Description | Max Score | Total Score | Query Cover | E-Value | Max Ident |
|---|---|---|---|---|---|---|
| CY062191.1A/ | New York/3251/2010 (H1N1) | 213 | 213 | 95% | $2.00 \times 10^{-52}$ | 99% |
| CY061591.1A/ | Texas/JMS403/2009(H1N1) | 213 | 213 | 95% | $2.00 \times 10^{-52}$ | 99% |

Whereas the invention has been described above in the context of multiple representative embodiments, it is not limited to those embodiments. On the contrary, it is intended to encompass all modifications, alternatives, and equivalents as may be within the spirit and scope thereof, as defined by the appended claims.

What is claimed is:

1. An apparatus, comprising:
a movement and placement device defining a preset motion range in at least two of x-, y-, and z-dimensions;
a microdroplet-manipulating device coupled to and movable by the controlled movement and placement device in the preset range;
a superhydrophobic surface located in the preset range;
a temperature-controlled vessel located in the preset range and comprising:
multiple interconnected chambers each chamber comprising a respective volume of a hydrophobic liquid held at a respective temperature; and
a plurality of open-top channels interconnecting the chambers, each channel comprising a respective volume of the hydrophobic liquid; and
a controller operably connected to the movement and placement device and to the microdroplet-manipulating device, the controller programmed to:
command the movement and positioning device to place the microdroplet-manipulating device relative to the superhydrophobic surface, and
command the movement and placement device to perform automatically at least one of:
(a) placing an aqueous liquid microdroplet on the superhydrophobic surface,
(b) manipulating the microdroplet on the superhydrophobic surface, or
(c) removing at least a portion of the microdroplet from the superhydrophobic surface; and
at least one of:
(d) placing the microdroplet in a first chamber of the temperature-controlled vessel,
(e) manipulating the microdroplet in the first chamber, or
(f) removing at least a portion of the microdroplet from the first chamber.

2. The apparatus of claim 1, wherein the microdroplet-manipulating device comprises a syringe fitted with a tip.

3. The apparatus of claim 2, wherein the controller is programmed to cause the syringe, whenever the microdroplet is in a chamber of the vessel and submerged in the hydrophobic liquid:
to hold the microdroplet in a pendant manner from the tip and
to move the microdroplet relative to the hydrophobic liquid.

4. The apparatus of claim 2, wherein the microdroplet-manipulating device further comprises a vibration-producing device disposed in contact with the syringe so as to, when actuated, vibrate the syringe in an orbital manner sufficiently to impart a corresponding stirring motion of the microdroplet in contact with the tip.

5. The apparatus of claim 1, wherein the vessel comprises a first chamber containing a hydrophobic liquid held at a nucleic acid-denaturation temperature, a second chamber containing the hydrophobic liquid held at a nucleic acid-annealing temperature, and a third chamber containing the hydrophobic liquid held at a nucleic acid-extending temperature.

6. The apparatus of claim 5, wherein:
the microdroplet-manipulating device comprises a syringe fitted with a tip; and
the controller is programmed to cause the syringe to retract the microdroplet into the tip whenever the microdroplet is being moved, by respective motion of the syringe imparted by the movement and placement device, through at least one of the plurality of channels from one chamber to the next.

7. The apparatus of claim 1, wherein the controller is programmed to execute at least two protocols on a microdroplet, the protocols including a first protocol comprising at least one step performed with the microdroplet on the superhydrophobic surface and a second protocol comprising at least one step performed with the microdroplet in the vessel submerged in the hydrophobic liquid.

8. The apparatus of claim 7, wherein the first protocol is directed to at least one of releasing genetic material from cells in the microdroplet, diluting the microdroplet, centrifuging the microdroplet, lysing the microdroplet, precipitating genetic material in the microdroplet, collecting genetic material from the microdroplet, washing and drying collected genetic material from the microdroplet, and rehydrating collected genetic material from the microdroplet.

9. The apparatus of claim 8, wherein:
the microdroplet-manipulating device comprises a syringe fitted with a tip;
the first protocol is directed to at least collecting genetic material from the microdroplet; and
collecting genetic material from the microdroplet comprises adhering the genetic material to the tip.

10. The apparatus of claim 9, wherein collecting genetic material further comprises rotating the tip as the genetic material adheres to the tip.

11. The apparatus of claim 5, wherein the controller is programmed to command the movement and placement device to perform the recited acts of:
(c) removing at least a portion of the microdroplet from the superhydrophobic surface,
(d) placing the microdroplet in a chamber of the temperature-controlled vessel, and
(e) manipulating the microdroplet in the chamber; and
wherein the controller is further programmed to command the movement and placement device to place the microdroplet-manipulating device proximate to the chambers of the vessel in a cyclic manner at respective times, each cycle comprising:
locating the microdroplet-manipulating device proximate to the first chamber of the vessel at which the microdroplet-manipulating device submerges a microdroplet being carried by the microdroplet-manipulating device in the hydrophobic liquid in the first chamber for a first defined length of time;
transporting the microdroplet through to the second chamber through a first one or the plurality of channels, while keeping the droplet submerged in the hydrophobic liquid;
holding the microdroplet in the hydrophobic liquid in the second chamber for a second defined length of time;
transporting the microdroplet to the third chamber through a second one of the plurality of channels, while keeping the droplet submerged in the hydrophobic liquid;
holding the microdroplet in the hydrophobic liquid in the third chamber for a third defined length of time; and
returning the microdroplet to the first chamber through a third one of the plurality of channels, while keeping the droplet submerged in the hydrophobic liquid;
wherein the cycle is commanded to be repeated a plurality of times.

12. The apparatus of claim 5, wherein the controller is programmed to command the movement and placement device to perform each of the recited acts of:

(c) removing at least a portion of the microdroplet from the superhydrophobic surface,
(d) placing the microdroplet in a chamber of the temperature-controlled vessel, and
(e) manipulating the microdroplet in the chamber.

13. The apparatus of claim 12, wherein the controller is programmed to command the movement and placement device to place the microdroplet-manipulating device proximate to the chambers of the vessel in a cyclic manner at respective times, each cycle comprising:
locating the microdroplet-manipulating device proximate to the first chamber of the vessel at which the microdroplet-manipulating device submerges a microdroplet being carried by the microdroplet-manipulating device in the hydrophobic liquid in the first chamber for a first defined length of time;
transporting the microdroplet through to the second chamber through a first one or the plurality of channels, while keeping the droplet submerged in the hydrophobic liquid;
holding the microdroplet in the hydrophobic liquid in the second chamber for a second defined length of time;
transporting the microdroplet to the third chamber through a second one of the plurality of channels, while keeping the droplet submerged in the hydrophobic liquid;
holding the microdroplet in the hydrophobic liquid in the third chamber for a third defined length of time; and
returning the microdroplet to the first chamber through a third one of the plurality of channels, while keeping the droplet submerged in the hydrophobic liquid;
wherein the cycle is commanded to be repeated a plurality of times.

14. The apparatus of claim 5, wherein the controller is programmed to command the movement and placement device to perform each of the recited acts of:
(d) placing the microdroplet in the first chamber of the temperature-controlled vessel,
(e) manipulating the microdroplet in the first chamber, and
(f) removing at least a portion of the microdroplet from the first chamber.

15. A method, comprising:
providing a movement and placement device defining a preset motion range in at least two of x-, y-, and z-dimensions;
providing a microdroplet-manipulating device coupled to and movable by the controlled movement and placement device in the preset range;
providing a superhydrophobic surface located in the preset range;
providing a temperature-controlled vessel located in the preset range, the vessel comprising:
multiple interconnected chambers, each chamber comprising a respective volume of a hydrophobic liquid held at a respective temperature, and
a plurality of open-top channels interconnecting the chambers, each channel comprising a respective volume of the hydrophobic liquid;
providing a controller operably connected to the movement and placement device and to the microdroplet-manipulating device, the controller being programmed to:
command the movement and positioning device to place the microdroplet-manipulating device relative to the superhydrophobic surface, and
command the movement and placement device to perform automatically at least one of:
(a) placing an aqueous liquid microdroplet on the superhydrophobic surface,
(b) manipulating the microdroplet on the superhydrophobic surface, or
(c) removing at least a portion of the microdroplet from the superhydrophobic surface; and
at least one of:
(d) placing the microdroplet in a first chamber of the temperature-controlled vessel,
(e) manipulating the microdroplet in the first chamber, or
(f) removing at least a portion of the microdroplet from the first chamber;
placing an amount of a sample in contact with the superhydrophobic surface using the microdroplet-manipulating device coupled to a movement and placement device defining a preset motion range in at least two of x-, y-, and z-dimensions to form at least one microdroplet of the sample on the superhydrophobic surface; and
performing at least one step of a first protocol on, in, or with the microdroplet on the superhydrophobic surface.

16. The method of claim 15, wherein the at least one step is selected from the group consisting of:
moving the microdroplet on the superhydrophobic surface,
adding a substance to the microdroplet on the superhydrophobic surface,
removing a substance from the microdroplet on the superhydrophobic surface,
mixing contents of the microdroplet on the superhydrophobic surface,
concentrating the microdroplet on the superhydrophobic surface,
agitating the microdroplet on the superhydrophobic surface,
changing a volume of the microdroplet on the superhydrophobic surface,
changing a shape of the microdroplet on the superhydrophobic surface,
changing a density of the microdroplet on the superhydrophobic surface,
changing a composition of the microdroplet on the superhydrophobic surface,
changing a position of the microdroplet on the superhydrophobic surface,
holding a substance relative to the microdroplet on the superhydrophobic surface,
merging the microdroplet with another microdroplet on the superhydrophobic surface,
splitting the microdroplet on the superhydrophobic surface, and
rotating the microdroplet on the superhydrophobic surface.

17. The method of claim 15, further comprising:
removing at least part of the microdroplet from the superhydrophobic surface using the microdroplet-manipulating device;
placing the removed at least part of the microdroplet in contact with a hydrophobic liquid, using the microdroplet-manipulating device, to form a second microdroplet in the hydrophobic liquid; and
performing at least one step of a second protocol on, in, or with the second microdroplet in the hydrophobic liquid.

18. The method of claim 17, wherein:
the second protocol is a thermocycling protocol; and
the at least one step of the second protocol comprises keeping the second microdroplet immersed in the hydrophobic liquid at a specified temperature for a specified period of time.

19. The method of claim 15, wherein the microdroplet-manipulating device comprises a syringe fitted with a tip.

20. The method of claim 19, wherein the controller is programmed to cause the syringe, whenever the microdroplet is in a chamber of the vessel and submerged in the hydrophobic liquid:
to hold the microdroplet in a pendant manner from the tip, and
to move the microdroplet relative to the hydrophobic liquid.

21. The method of claim 19, wherein the microdroplet-manipulating device further comprises a vibration-producing device disposed in contact with the syringe so as to, when actuated, vibrate the syringe in an orbital manner sufficiently to impart a corresponding stirring motion of the microdroplet in contact with the tip.

22. The method of claim 15, wherein the multiple interconnected chambers comprise a first chamber comprising a hydrophobic liquid held at a nucleic acid-denaturation temperature, a second chamber comprising the hydrophobic liquid held at a nucleic acid-annealing temperature, and a third chamber comprising the hydrophobic liquid held at a nucleic acid-extending temperature.

23. The method of claim 22, wherein:
the microdroplet-manipulating device comprises a syringe fitted with a tip; and
the controller is programmed to cause the syringe to retract the microdroplet into the tip whenever the microdroplet is being moved, by respective motion of the syringe imparted by the movement and placement device, through at least one of the plurality of channels from one chamber to the next.

24. The method of claim 15, wherein the first protocol is directed to at least one of: releasing genetic material from cells in the microdroplet, diluting the microdroplet, centrifuging the microdroplet, lysing the microdroplet, precipitating genetic material in the microdroplet, collecting genetic material from the microdroplet, washing and drying collected genetic material from the microdroplet, or rehydrating collected genetic material from the microdroplet.

25. The method of claim 24, wherein:
the microdroplet-manipulating device comprises a syringe fitted with a tip; and
the first protocol is directed to at least collecting genetic material from the microdroplet; and
collecting genetic material from the microdroplet comprises adhering the genetic material to the tip.

26. The method of claim 25, wherein the collecting the genetic material further comprises rotating the tip as the genetic material adheres to the tip.

* * * * *

UNITED STATES PATENT AND TRADEMARK OFFICE
CERTIFICATE OF CORRECTION

PATENT NO. : 9,719,134 B2
APPLICATION NO. : 14/512256
DATED : August 1, 2017
INVENTOR(S) : Jeong-Yeol Yoon and David J. You It is certified that error appears in the above-identified patent and that said Letters Patent is hereby corrected as shown below:

In the Specification

Column 5, Line 67, "The can also" should read --They can also--.

Column 6, Line 8, "are surprising result obtained" should read --are surprising results obtained--.

Column 6, Line 12, "stifling" should read --stirring--.

Column 11, Line 33, "to using of" should read --to use of--.

Column 13, Line 53, "configure to" should read --configured to--.

Column 16, Line 16, "protocol." should read --protocol).--.

Column 16, Lines 56-57, "can be is drawn" should read --can be drawn--.

Column 26, Lines 53-54, "could (and was) replaced" should read --could be (and was) replaced--.

Column 27, Line 21, "stifling" should read --stirring--.

Column 29, Lines 31-32, "(~1500 bp), and corresponding" should read --(~1500 bp), a corresponding--.

Signed and Sealed this
Fourth Day of June, 2019

Andrei Iancu
*Director of the United States Patent and Trademark Office*

```
                         SEQUENCE LISTING

<160> NUMBER OF SEQ ID NOS: 4

<210> SEQ ID NO 1
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 1
gggaattcgt cgacgtgtct gaactgtctc aatt                                  34

<210> SEQ ID NO 2
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 2
gagccgaagc ttttacttcg ccggaatttc tt                                    32

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
cagtccgaaa gaggcgaag                                                   19

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
gaaagcttgc cctcaatgca g                                                21
```